(12) United States Patent
Amoroso et al.

(10) Patent No.: US 7,442,800 B2
(45) Date of Patent: Oct. 28, 2008

(54) NUCLEOPHILIC HETEROCYCLIC CARBENE DERIVATIVES OF PD(ACAC)₂ FOR CROSS-COUPLING REACTIONS

(75) Inventors: Dino Amoroso, Medina, OH (US); Andrew Bell, Lakewood, OH (US); Oscar Navarro Fernandez, Brighton, MA (US); Steven P. Nolan, New Orleans, LA (US); Nicolas Marion, Tarragona (ES)

(73) Assignee: Promerus LLC, Brecksville, OH (US)

( * ) Notice: Subject to any disclaimer, the term of this patent is extended or adjusted under 35 U.S.C. 154(b) by 0 days.

(21) Appl. No.: 11/441,825

(22) Filed: May 26, 2006

(65) Prior Publication Data

US 2006/0287544 A1  Dec. 21, 2006

Related U.S. Application Data

(60) Provisional application No. 60/788,989, filed on Apr. 4, 2006, provisional application No. 60/685,620, filed on May 27, 2005.

(51) Int. Cl.
*C07F 15/00* (2006.01)

(52) U.S. Cl. .......................... 548/101; 544/225; 546/2; 556/137

(58) Field of Classification Search ................. 548/101; 546/2; 544/225; 556/137
See application file for complete search history.

(56) References Cited

U.S. PATENT DOCUMENTS

| | | | | |
|---|---|---|---|---|
| 3,231,595 | A * | 1/1966 | Brotherton et al. | 560/354 |
| 5,703,269 | A | 12/1997 | Herrmann et al. | |
| 6,316,380 | B1 | 11/2001 | Nolan et al. | |
| 6,531,607 | B2 * | 3/2003 | Goossen et al. | 548/103 |
| 6,774,274 | B2 | 8/2004 | Nolan et al. | |
| 6,888,029 | B2 | 5/2005 | Buchwald et al. | |
| 2001/0056190 | A1 * | 12/2001 | Goossen et al. | 548/101 |
| 2003/0149273 | A1 * | 8/2003 | Militzer et al. | 548/101 |
| 2004/0242947 | A1 * | 12/2004 | Beller et al. | 585/527 |
| 2005/0154205 | A1 * | 7/2005 | Militzer et al. | 546/2 |
| 2006/0122398 | A1 * | 6/2006 | Karch et al. | 548/101 |
| 2006/0229448 | A1 * | 10/2006 | Stahl et al. | 540/541 |
| 2007/0004917 | A1 * | 1/2007 | Bertrand et al. | 546/2 |
| 2007/0073055 | A1 * | 3/2007 | Organ et al. | 540/541 |

OTHER PUBLICATIONS

Lebel et al., Journal of American Chemical Society, vol. 126, No. 16, pp. 5046-5047 (2004).*
Viciu, Mihai S. et al., "Activation and Reactivity of (NHC)Pd(allyl)Cl (NHC=N-Heterocyclic Carbene) . . . " Organometallics 2002, pp. 5470-5472, vol. 21, No. 25.
Navarro, Oscar et al., "Cross-Coupling and Dehalogenation Reactions Catalyzed by (N-Heterocyclic carbene)Pd(allyl)Cl . . . " J. Org. Chem. 2004, pp. 3173-3180, vol. 69, No. 9.
Hillier, Anna C. et al., "Palladium/Nucleophilic Carbene Catalysts for Cross-Coupling Reactions" Platinum Metals Rev. 2002, pp. 50-64, vol. 46, No. 2.
Hillier, Anna C. et al. "Catalytic Cross-Coupling Reactions Mediated by Palladium/Nucleophilic Carbene Systems" J. Org. Chem. 2002, pp. 69-82, vol. 653.
Terao, Jun et al., "Pd-Catalyzed Cross-Coupling Reaction of Alkyl Tosylates and Bromides with Grignard Reagents . . . " Chemistry Letters 2003, pp. 890-891, vol. 32, No. 10.
Grasa, Babriela A. et al., "Catalytic Activity of Pd(II) and Pd(II)/DAB-R Systems for the Heck Arylation of Olefins" J. Org. Chem. 2003, pp. 269-279, vol. 687.
Gooben, Lukas J. et al., "A New Practical Ketone Synthesis Directly from Carboxylic Acids: First Application of Coupling Reagents . . . " Chem. Commun. 2001, pp. 2084-2085.
Zhang, Chunming et al., "Palladium-Imidazol-2-ylidene Complexes as Catalysts for Facile and Efficient Suzuki . . . " J. Org. Chem. 1999, pp. 3804-3805, vol. 64., No. 11.
Huang, Jinkun et al., "Efficient Cross-Coupling of Aryl Chlorides with Aryl Grignard Reagents . . . " J. Am. Chem. Soc. 1999, pp. 9889-9890, vol. 121., No. 4.

* cited by examiner

*Primary Examiner*—P. Nazario Gonzalez
(74) *Attorney, Agent, or Firm*—The Webb Law Firm

(57) ABSTRACT

Embodiments in accordance with the present invention provide for a palladium complex characterized by the general formula:

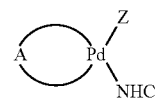

where A is a bidentate monoanionic ligand, NHC is a nucleophilic heterocyclic carbene, and Z is an anionic ligand. Such palladium complexes are useful in initiating cross-coupling reactions.

39 Claims, 1 Drawing Sheet

US 7,442,800 B2

NUCLEOPHILIC HETEROCYCLIC CARBENE DERIVATIVES OF PD(ACAC)$_2$ FOR CROSS-COUPLING REACTIONS

CROSS-REFERENCE TO RELATED APPLICATIONS

This application claims the benefits of U.S. Provisional Application No. 60/788,989, filed Apr. 4, 2006 and U.S. Provisional Application No. 60/685,620, filed May 27, 2005, both of which applications are herein incorporated by reference in their entirety.

TECHNICAL FIELD

The present invention relates generally to palladium complexes having a bidentate monoanionic ligand, a nucleophilic heterocyclic carbene (NHC), and an anionic ligand used in carbon-carbon and carbon-heteroatom bond forming reactions, as well as methods for making such complexes.

BACKGROUND

Palladium catalyzed carbon-carbon and carbon-heteroatom bond forming reactions, also referred to hereinafter as cross-coupling reactions, such as but not limited to conventional reactions such as Suzuki-Miyaura, Stille, Heck, Sonagashira, Negishi, Kumada cross-coupling, Buchwald-Hartwig aminations, catalytic ether formation, catalytic α-arylations of ketones, and catalytic thioether formation reactions, are extremely powerful synthetic tools in organic chemistry.

However, there are major limitations associated with the use of such reactions that would be advantageous to overcome. One such limitation is that traditional catalysts, such as palladium tetrakis(triphenylphosphine) or the catalysts formed in situ from an appropriate triarylphosphine and either a Pd(II) or Pd(0) precursor, have a generally low activity and therefore need to be present in comparatively high concentrations to realize high conversion rates. Both the high cost of palladium and the high costs associated with removing palladium metal residues due to spent catalyst in the product make the use of such high concentrations undesirable. Another limitation is that such traditional catalysts exhibit even lower activity in cross-coupling reactions that employ deactivated aryl bromides and are generally ineffective with respect to coupling aryl chlorides. As aryl chlorides are a particularly attractive class of substrate due to their greater availability and attractive costs, as compared to their bromide and iodide analogs, the ineffectivity of such traditional catalysts is problematic.

Research focusing on palladium compounds and their use in catalysis at both industrial and laboratory scales has increased over the past ten years. Ligandless systems are known and have been studied, however it is well understood that the ancillary ligation to the metal center plays a crucial role in dictating the efficiency of a catalytic system, thus such ligandless systems have not been particularly effective. As a result, bulky, electron-rich phosphines ligands such as P(t-Bu)$_2$Me and P(t-Bu)$_3$ have come to be commonly used to stabilize Pd(0) intermediates and hence have been seen to be effective. However, phosphine ligands have several drawbacks:

(1) they often are prone to air oxidation and therefore require air-free handling,
(2) when these ligands are subjected to higher temperatures, significant P—C bond degradation occurs, thus requiring the use of an excess of the phosphine, and
(3) they often react with Pd precursors, such as Pd(OAc)$_2$, in a reduction process forming P$_n$Pd(0) and phosphine oxide;

which limit their usefulness.

As they represent an attractive alternative to tertiary phosphines in homogeneous catalysis, nucleophilic heterocyclic carbene (NHC) ligands have become increasingly popular in the last few years. In general, NHCs exhibit reaction behavior that is much different than phosphines, for example, displaying high thermal stability and tolerance to oxidation conditions. Several systems based on the combination of imidazolium salts (air-stable precursors to air sensitive NHC) and Pd(0) or Pd(II) sources have been developed to generate catalytically active species in situ, where such active species mediate numerous organic reactions, principally cross-coupling reactions. These preliminary systems and others have demonstrated the importance of the NHC/Pd ratio on the efficiency of the reactions, pointing to an optimum 1:1 ligand to metal ratio in most cases. From there, efforts have been aimed at the development of monomeric NHC-bearing Pd(II) complexes and the study of their catalytic activity. Generally, shorter reaction times are observed in these well-defined systems, since the carbene is already coordinated to the palladium center. Also, the use of a well-defined pre-catalyst allows for a better knowledge of the amount of ligand-stabilized palladium species in solution, by reducing the possibility of side reactions leading to ligand or palladium precursor decomposition prior to the coordination of the ligand.

The synthesis of monomeric (NHC)Pd(allyl)Cl complexes and (NHC)Pd(carboxylate) complexes have been reported among many architectures, and activation mechanisms and catalytic activities have been studied. The synthesis of most of these complexes is directly related to successful in situ systems involving the use of air sensitive NHCs and a corresponding palladium source. For example, a catalytic system for the Heck reaction involving the use of diazabutadiene ligands and Pd(OAc)$_2$ or Pd(acac)$_2$ as palladium precursors has been reported.

2,4-Pentadione (acetylacetone, Hacac) and other β-carbonyl compounds are very versatile and are common ligands in transition metal chemistry since they are generated on an industrial scale. 2,4-Pentadione typically binds metal ions in a η$^2$—O,O fashion, although some other coordination modes have been observed in platinum (II) and palladium(II) complexes. Previous work has focused on the reactivity of palladium(II) acetylacetonate and related compounds with phosphines leading to new complexes, but no catalytic applications were reported. Recently, others have extensively researched the use of such types of complexes as hydrogenation catalysts.

Thus, the use of currently known catalyst systems for carbon-carbon and carbon-heteroatom formation can often be problematic. Such issues include (i) relatively difficult or laborious synthesis, (ii) expensive catalyst precursors and/or ligand sets, (iii) oxygen and water sensitivity of ligands or metal catalysts, (iv) optimization of activity is difficult because of disparate pre-catalyst structures and unusual and non-modular ligands, and (v) catalysts for the activation of aryl chloride need to be used in relative high concentrations. Therefore, it would be desirable to have catalysts or catalyst systems that provide solutions to the above-identified problems. It would also be desirable if such catalyst systems could be used directly on the industrial scale without the need for their isolation and are stable over wide ranges of temperature and pressure. Further, it would be desirable if such complexes could be prepared in a single reaction step from readily available starting materials.

DETAILED DESCRIPTION

Figure 1:
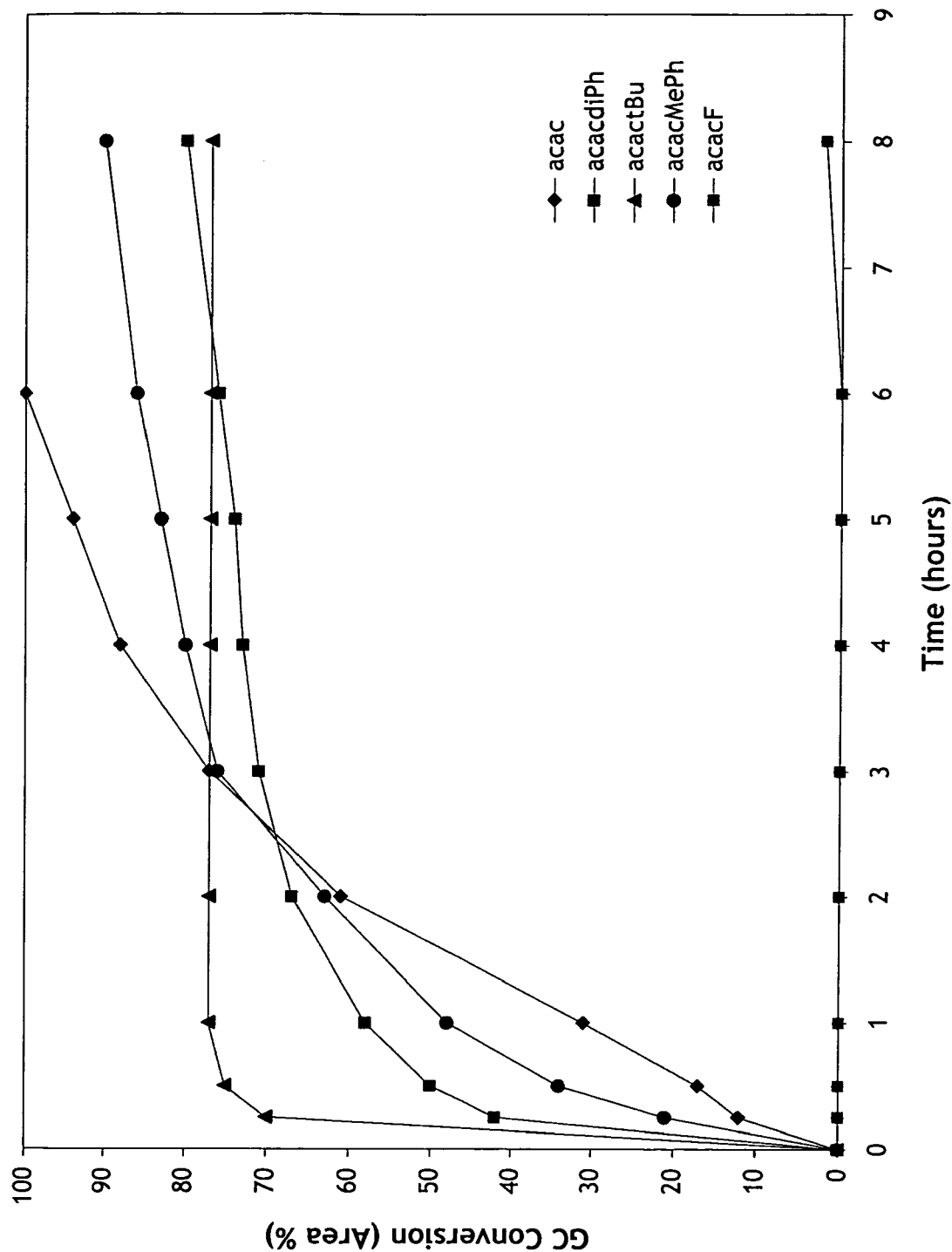
FIG. 1 is a graph of percent conversion versus time for the procedure described in Example 47.

Other than in the operating examples, or where otherwise indicated, all numbers, values and/or expressions referring to quantities of ingredients, reaction conditions, etc., used in the specification and claims are to be understood as modified in all instances by the term "about."

Various numerical ranges are disclosed-in this patent application. Because these ranges are continuous, unless specifically noted otherwise, they include the minimum and maximum values of each range and every value therebetween. Furthermore, unless expressly indicated otherwise, the various numerical ranges specified in this specification and in the claims are approximations that are reflective of the various uncertainties of measurement encountered in obtaining such values.

As used above, and throughout the specification, the following terms, unless otherwise indicated, will be understood to have the meanings provided below.

By "cross-coupling" is meant as a reaction or series of reactions which result in the formation of new carbon-carbon or carbon-heteroatom bonds.

By "hydrocarbyl" is meant that the substituent is hydrogen or is composed solely of carbon and hydrogen atoms. As one skilled in the art knows, hydrocarbyl is inclusive of the following where the definitions apply regardless of whether a term is used by itself or in combination with other terms, unless otherwise indicated. Therefore, the definition of "alkyl" applies to "alkyl" as well as the "alkyl" portions of "aralkyl", "alkaryl", etc.

As used herein, the term "alkyl" means an aliphatic hydrocarbon group that can be linear or branched acyclic or cyclic and comprises 1 to 25 carbon atoms in the chain. In one embodiment, useful alkyl groups comprise 1 to 12 carbon atoms in the chain. "Branched" means that one or more lower alkyl groups such as methyl, ethyl or propyl, are attached to a linear alkyl chain. The alkyl group can contain one or more heteroatoms selected from F, O, N, and Si. Non-limiting examples of suitable alkyl groups include methyl, ethyl, n-propyl, isopropyl, n-butyl, t-butyl, n-pentyl, hexyl, heptyl, nonyl, decyl, cyclohexyl and cyclopropylmethyl.

"Aryl" means an aromatic monocyclic or multicyclic ring system comprising 5 to 14 carbon atoms, preferably 6 to 10 carbon atoms. The aryl group can contain one or more heteroatoms selected from F, O, N and Si. The aryl group can be substituted with one or more "ring system substituents" which may be the same or different, and include hydrocarbyl substituents. Non-limiting examples of suitable aryl groups include phenyl, naphthyl, indenyl, tetrahydronaphthyl and indanyl.

"Aralkyl" or "arylalkyl" means an aryl-alkyl-group in-which both aryl and alkyl are as previously described. In some embodiments, useful aralkyls comprise a lower alkyl group. Non-limiting examples of such suitable aralkyl groups include benzyl, phenethyl and naphthlenylmethyl where the aralkyl is linked to the norbornene through the alkylene group. In some embodiments, the aralkyl group can contain one or more heteroatoms selected from F, O, N and Si.

"Cyclic alkyl" or cycloalkyl means a non-aromatic mono- or multicyclic ring system generally encompassing 3 to 10 carbon atoms, in some embodiments 5 to 10 carbon atoms and in other embodiments 5 to 7 carbon atoms. The cycloalkyl can be substituted with one or more "ring system substituents" which may be the same or different, and include hydrocarbyl or aryl substituents. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornyl, adamantyl and the like.

As used herein, terms BPin, BCat, and 9-BBN mean:

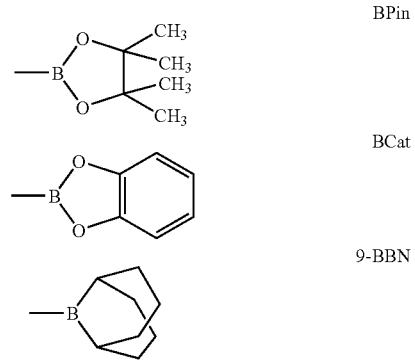

Embodiments in accordance with the present invention provide simple to synthesize catalysts or catalyst systems for carbon-carbon and carbon-heteroatom bond forming reactions. Such catalysts are advantageously based on inexpensive, commercially available, and stable precursors. Additionally, they are oxygen and water stable, are based on a structural class of compounds and ligands that can be readily modified to optimize such cross-coupling reactions for use with any particular class of substrates, and can activate aryl chloride substrates for use in such reactions while requiring only relatively low catalyst concentrations.

According to some embodiments in accordance with the present invention, a Pd (palladium) complex, generically represented by Formula I, is provided:

Formula I where A is a bidentate monoanionic ligand represented by Formula II, below:

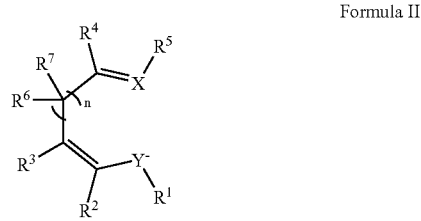

Formula II where each of X and Y are independently selected from O, N, or S and where $R^1$, $R^2$, $R^3$, $R^4$, $R^5$, $R^6$ and $R^7$ independently represent hydrogen, methyl, linear or branched $C_2$-$C_{10}$ alkyl, $C_3$-$C_{10}$ cycloalkyl, $C_7$-$C_{20}$ aralkyl, or $C_6$-$C_{24}$ aryl or substituted aryl, n represents an integer of 0, 1, or 2; NHC is a nucleophilic heterocyclic carbene; and Z is an anionic ligand, subject to the proviso that when either X or Y are O or S, $R^1$ and $R^5$, respectively, do not exist.

Further, $R^2$ and $R^3$ and the carbons to which they are attached or $R^4$ and $R^5$ and the carbon and X to which they are respectively attached can form a substituted or unsubstituted aromatic ring.

In some representations of Formulae I and II, X—Y is a bidentate monoanionic ligand, i.e., a chelate characterized by the presence of bonds from two bonding sites within the same ligand to a central metal atom, or a hemilabile group or ligand, i.e., a chelate characterized by the presence of bonds from two bonding sites within the same ligand to a central metal atom, wherein one of the bonds is readily broken by solvent to render a metal center bound to one terminus of the anionic group and thereby generating a vacant coordination site at the metal center. NHC is a nucleophilic heterocyclic carbene, that is to say a species capable of providing electron density to the metal center, i.e., donation of a pair of electrons. Z is selected from Cl, Br, I, OAc, OMs, OTf, OTs, $O_2CCF_3$, acetylacetonate (acac), trifluoroacetylacetonate, hexafluoroacetylacetonate (hfacac); dibenzoylmethanate (dbm), benzoylacetonate (bac), and tetramethylheptanedionate (tmhd).

In Formula II, the bidentate anionic species X—Y⁻ is generated from the neutral species HX–Y The groups X and Y are selected from O, N, or S, where $R^1$ through $R^5$ are as defined above. In the formula below, exemplary X—Y ligands are β-diketonato (O—O), β-diketiminato (N—N), β-ketiminato (N—O) and Schiff base (N—O) ligands. Thus the bidentate anionic species exists in tautomeric forms as shown below:

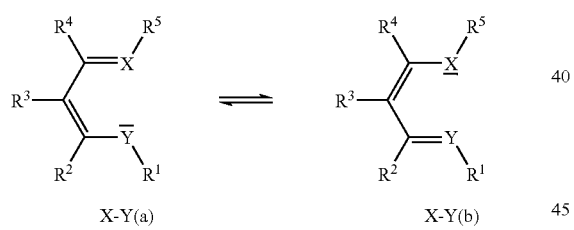

X-Y(a)        X-Y(b)

In other embodiments of the present invention, the bidentate anion X—Y is selected from:

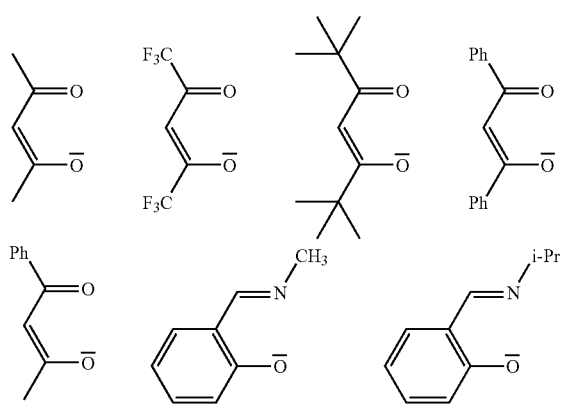

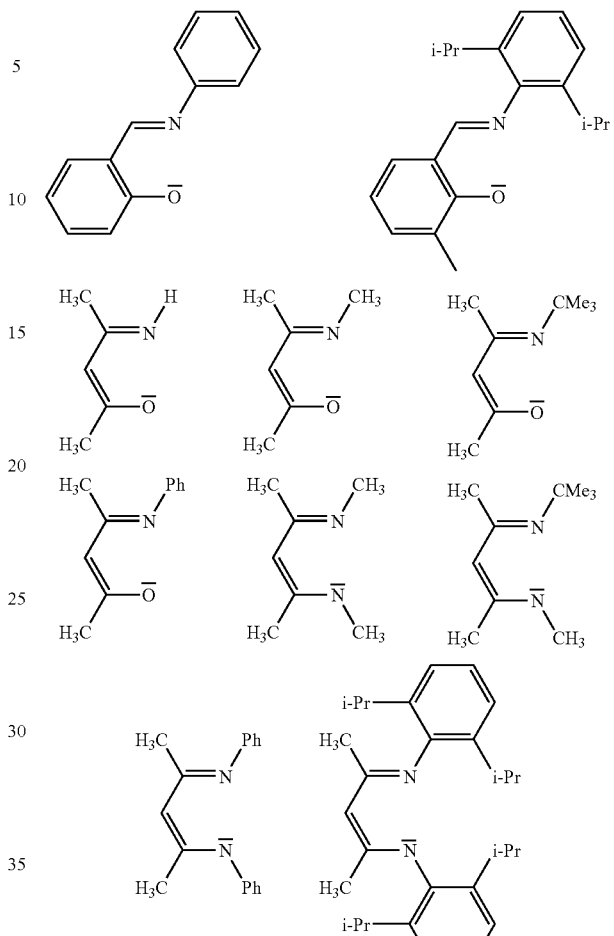

In still other embodiments the bidentate anion is one of the tropolone derivatives shown below or a derivative of any other appropriate substituted or unsubstituted hydrocarbyl.

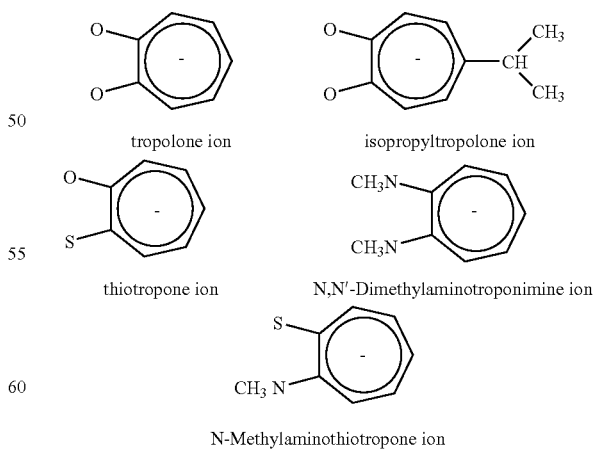

tropolone ion        isopropyltropolone ion thiotrope ion        N,N'-Dimethylaminotroponimine ion N-Methylaminothiotropone ion In some embodiments of the present invention, the palladium source and X—Y sources are selected from Pd(acac)$_2$, bis(trifluoroacetylacetonate)Pd, bis (hexafluoroacetylacetonate)Pd; bis (dibenzoylmethanate)Pd, bis (benzoylacetonate) Pd, bis(tetramethylheptanedionate)Pd, or bis(tropolonato) palladium (II).

In some embodiments in accordance with the invention, the nucleophilic heterocyclic carbene (NHC) is selected from Formulae A, B or C:

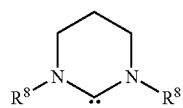

A

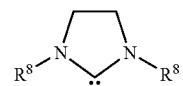

B

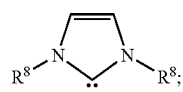

C where $R^8$ is independently selected from hydrogen, alkyl, substituted alkyl, cycloalkyl, substituted cycloalkyl, aryl, or substituted aryl.

In some embodiments, $R^8$ of Formula C is selected from methyl, ethyl, isopropyl, isobutyl, tert-butyl, cyclohexyl, norbornyl, adamantyl, 2,6-dimethylphenyl, 2,4,6-trimethylphenyl, 2,6-diisopropylphenyl, or 2-methylphenyl.

In yet other embodiments in accordance with the present invention, the carbene moiety is selected from (NHC)Pd(acac)$_2$, (NHC)Pd(acac)Cl, (NHC)Pd(hfacac)$_2$ (NHC)Pd(hfacac)Cl, (NHC)Pd(dbm)$_2$, (NHC)Pd(dbm)Cl, (NHC)Pd(tmhd)$_2$ (NHC)Pd(tmhd)Cl, (NHC)Pd(bac)$_2$ or (NHC)Pd(bac)Cl, where the NHC is selected from IMes (N,N'-bis(2, 4,6-trimethylphenyl)imidazol)-2-ylidene), sIMes (N,N'-bis (2,4,6-trimethylphenyl)-4,5-dihydroimidazol)-2-ylidene), IPr (N,N'-bis(2,6-diisopropylphenyl)imidazol)-2-ylidene), sIPr (N,N'-bis (2,6-diisopropylphenyl)-4,5-dihydroimidazol)-2-ylidene), IAd (N,N'-bis(adamantyl)imidazol-2-ylidene), ICy (N,N'-bis(cyclohexyl)imidazol-2-ylidene), or ItBu (N,N'-bis(tert-butyl)imidazol-2-ylidene).

In other embodiments of the present invention, specific complexes, (IPr)Pd(acac)$_2$ (Pd Complex 1) and (IPr)Pd(acac) Cl (Pd Complex 2), exhibit catalytic activity in the Buchwald-Hartwig aryl amination reaction and the α-ketone arylation reaction.

In comparison with the reported (PPh$_3$)Pd(acac)$_2$, a NHC-bearing analogue has been synthesized by the procedure of Scheme 1, shown below. Direct reaction of free carbene IPr with Pd(acac)$_2$ at room temperature in dry toluene yielded (IPr)Pd(acac)$_2$ (Pd Complex 1) in very high yield as a yellow powder. The presence of one oxygen-chelating ligand and one C-bound ligand in the complex was apparent by both $^{13}$C and 1H NMR. In the $^{13}$C NMR spectrum, 6 different signals above 160 ppm: 207.5 (C-bound acac), 192.9, 188.1, 185.6, 183.3 (carbonyl carbons) and 161.2 (carbenic carbon) were observed. In the $^1$H NMR spectrum, four methyl-proton singlet signals were observed each at 2.63, 2.01, 1.63 and 1.31, together with two signals at 5.90 and 4.78. The lowest-field methyl peaks are assigned to the carbon-bonded acac, together with the lowest-field methenic hydrogen, while the other three signals are assigned to the oxygen-chelating ligand. It is of note that the PPh$_3$ analogue showed only one peak for the methyls of the carbon bound ligand, due to free rotation. Clearly, the sterically demanding NHC ligand inhibits this rotation. The disposition of the ligands was unequivocally assigned when the crystal structure was resolved by X-ray diffraction. A square planar configuration around the palladium center can be observed, with nearly no distortion. As expected, the Pd—C carbenic distance is in the range of a single Pd—C bond. The Pd—O bond opposite to the NHC is elongated compared to the other Pd—O bond due to a strong trans effect.

Scheme 1. Synthetic path leading to (IPr)Pd(acac)$_2$(Pd Complex 1)

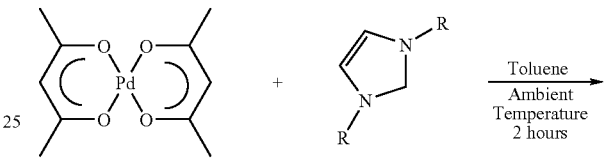

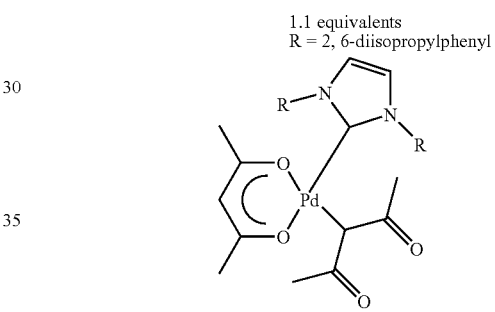

Pd Complex 1

Tests of the activity of Pd Complex 1 for the Buchwald-Hartwig reaction, using KOtBu as base and DME as solvent at 50° C. for the coupling of 4-chlorotoluene and morpholine, showed moderate catalyst activity (43% product in 1 hour with 1 mol % catalyst loading). The same moderate activity was observed for the coupling of 4-chlorotoluene and propiophenone using NaOtBu as base and toluene as solvent at 60° C. The reaction required 2 hours to reach completion using 1 mol % catalyst loading. The complex was modified with the idea of increasing the activity in catalysis.

The reaction of (PPh$_3$)Pd(acac)$_2$ with benzoyl chloride to yield the new species(PPh$_3$)Pd(acac)Cl has been reported, proposing a sequence of oxidative addition-reductive elimination reactions. In a similar way, Pd Complex 1 reacts with one equivalent of HCl at room temperature to produce the new species (IPr)Pd(acac)Cl (Pd Complex 2) as a yellow powder in nearly quantitative yield (Scheme 2). The loss of the C-bound ligand is again clearly evidenced by NMR. In $^{13}$C NMR, only two carbonyl carbons (187.1, 184.1) and the carbenic carbon (156.4) appear, whereas in $^1$H NMR, only one acac ligand can be assigned: singlet at 5.12, accounting for one hydrogen, and two methylic singlets (1.84, 1.82). Again, the structure features were unequivocally assigned when the structure was determined by single crystal X-ray diffraction. For this complex, the Pd—O distances are more similar (2.036, 2.044 Å), whereas the square planar coordination around the palladium center becomes slightly more distorted.

Scheme 2. Synthetic path leading to (IPr)Pd(acac)Cl(Pd Complex 2)

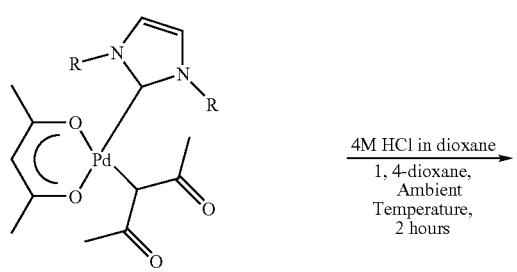

R = 2,6-diisopropylphenyl

4M HCl in dioxane
1, 4-dioxane,
Ambient
Temperature,
2 hours

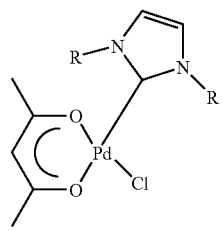

Pd Complex 2

While not being bound to any one theory, it is thought that the formation of Pd Complex 1 and the subsequent formation of Pd Complex 2 occur by the pathway illustrated in Scheme 3, shown below. Thus the coordination of the sterically demanding IPr by palladium is accompanied by the transition of one acac ligand from the η2-O,O-chelate to the O-monodentate form, with subsequent transformation to the π-hydroxoallyl form and further to the C-bonded form. Thus the oxidative addition of HCl to Complex 1, followed by reductive elimination of acacH yields Complex 2.

Scheme 3. Proposed Mechanism for the Formation of Pd Complexes 1 and 2

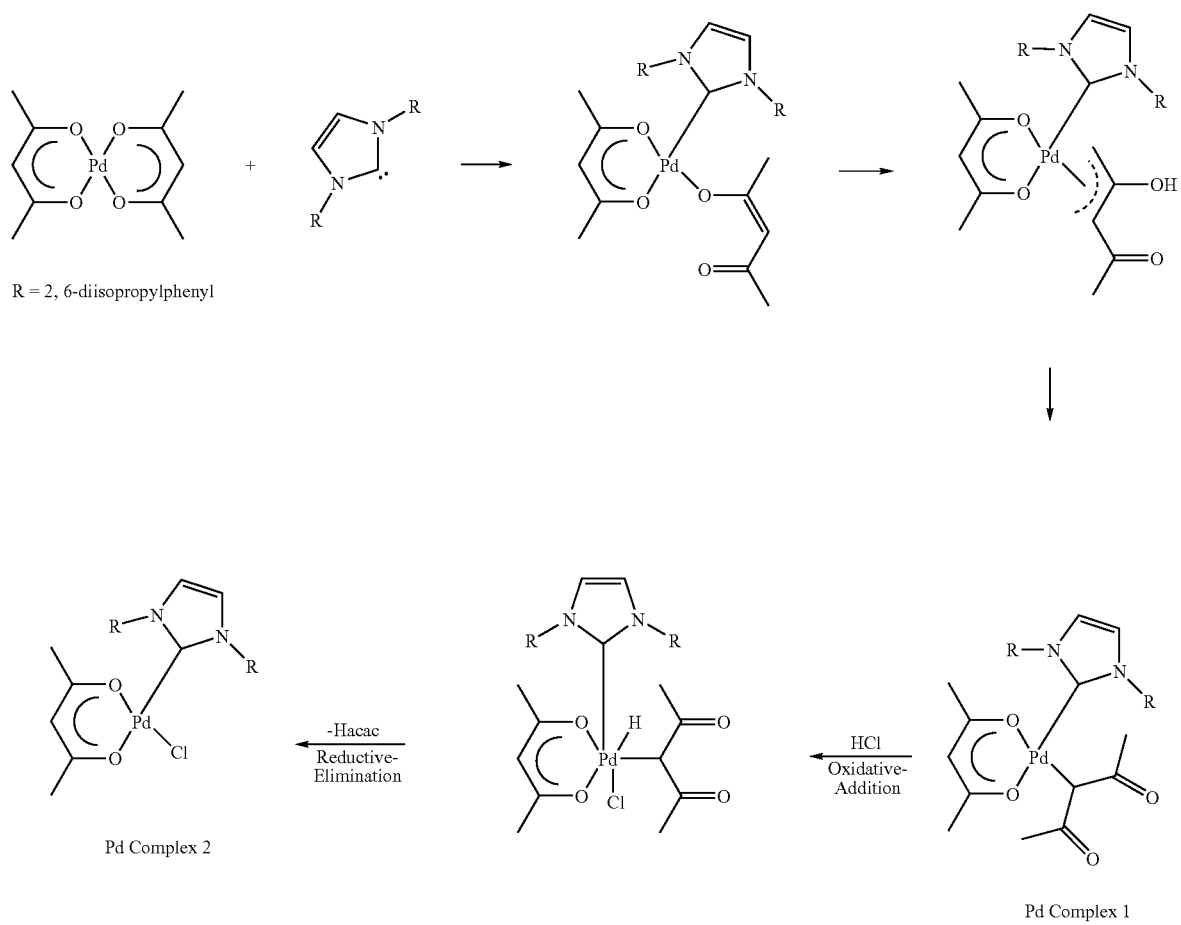

The activity of Pd Complex 2 for the Buchwald-Hartwig coupling reaction of morpholine and 4-chlorotoluene in the previously mentioned conditions was then tested. Using 1 mol % of Complex 2, the coupling occurred in 97% yield in only 30 minutes (Table 1, entry 1, isolated yield). Advantageously, the product could be obtained in good yield using low catalyst loading (0.1 mol %) or at room temperature where the reaction time was increased.

Results for the amination of aryl chlorides using Pd Compound 2 as catalyst are shown in Table 1. Various substrates were examined: heteroaromatic (entry 2), sterically demanding (entry 3) and deactivated chlorides (entry 4). The coupling of the stetically demanding dibutylamine with 4-chlorotoluene required a longer time (entry 5), and was the only reaction in which dehalogenation of the aryl chloride was observed (3 % by GC). As the synthesis of unsymmetrical tertiary amines starting with primary amines remains a challenge, the reaction between aniline and 2-chloropyridine was investigated. One-pot syntheses of N,N-bis(2-pyridyl)amino ligands, especially with aryl chlorides, are attractive due to the number of applications in which these compounds can take part: C—C bond formation, homogeneous and heterogeneous catalysis, DNA binding and nonlinear optical materials. The formation of the double pyridilation product was observed in good yield when 2.1 equivalents of the chloride were used (entry 6).

TABLE 1

Buchwald-Hartwig Aryl Amination of Aryl Chlorides Using Pd Complex 2

$$R\text{-Ar-Cl} + R'_2NH \xrightarrow[\text{DME, 1 mL}]{\text{1 mol \% KOtBu, 1.1 equiv}} R\text{-Ar-}NR'_2$$

1 mmol ; 1.1 mmol ; 50 °C

| | aryl chloride | amine | product | time (h) | yield (%)[1] |
|---|---|---|---|---|---|
| 1 | 4-chlorotoluene | morpholine | 4-(4-methylphenyl)morpholine | 0.5 | 97 |
| 2 | 2-chloropyridine | morpholine | 4-(2-pyridyl)morpholine | 0.5 | 98 |
| 3 | 2,6-dimethylchlorobenzene | morpholine | 4-(2,6-dimethylphenyl)morpholine | 1.5 | 90 |
| 4 | 4-chloroanisole | morpholine | 4-(4-methoxyphenyl)morpholine | 4 | 99 |
| 5 | 4-chlorotoluene | Bu$_2$NH | Bu$_2$N-(4-methylphenyl) | 6 | 95 |
| 6 | 2-chloropyridine | aniline | N,N-bis(2-pyridyl)aniline | 10 | 93[2] |

[1] Isolated yields, average of two runs.
[2] 2.1 equivalents of aryl chloride used.

As for the Buchwald-Hartwig reaction, Pd Complex 2 performed more effectively than did Pd Complex 1 for the α-ketone arylation reaction. The time for the coupling of propiophenone and 4-chlorotoluene (Table 2, entry 1) was reduced by half. Further, by using Pd Complex 2, the coupling of aryl-aryl and aryl-alkyl keytones with a variety of aryl chlorides was advantageously obtained.

Since Pd Complex 2 displays a higher activity than Pd Complex 1, the convenience of synthesizing Pd Complex 2 without the need of isolating the (IPr)Pd(acac)$_2$ intermediate would be desirable. To that effect, a multigram one-pot synthesis of Complex 2 was developed and such is summarized in Scheme 4, below. Reaction of the free carbene IPr with Pd(acac)$_2$ in dry 1,4-dioxane at room temperature, followed by the

TABLE 2

α-Ketone Arylation with Aryl Chlorides Using Pd Complex 2

| | aryl chloride | ketone | product | time (h) | yield (%)[1] |
|---|---|---|---|---|---|
| 1 | 4-chlorotoluene | propiophenone | | 1 | 97 |
| 2 | chlorobenzene | 1-acetonaphthone | | 10 | 70 |
| 3 | chlorobenzene | cyclohexanone | | 2 | 86 |
| 4 | 2,6-dimethylchlorobenzene | acetophenone | | 1 | 95 |
| 5 | 4-chloroanisole | acetophenone | | 1.5 | 92 |
| 6 | 3-chloropyridine | propiophenone | | 2 | 89 |

[1] Isolated yields, average of two runs.

addition of an equimolecular amount of HCl, leads to the formation of the desired product.

shown in Scheme 5, below. In this procedure the imidazoylium salt (N,N'-bis (2, 6-diisopropyl phenyl) imidazolium chloride) is deprotected in situ by the Pd(acac)$_2$ complex to generate NHC which binds to the metal center, a chloride anion which replaces the acac moiety, and free acetylacetonate. Advantageously, this synthetic method does not require the isolation of free NHC and the product exhibits acceptable air-stability.

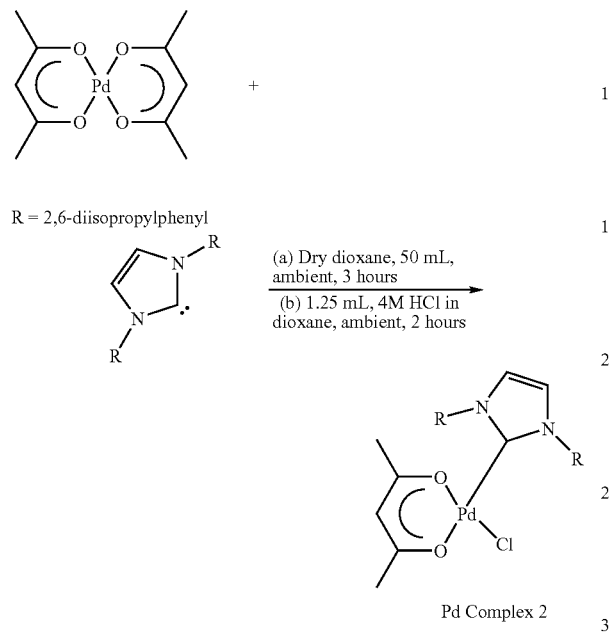

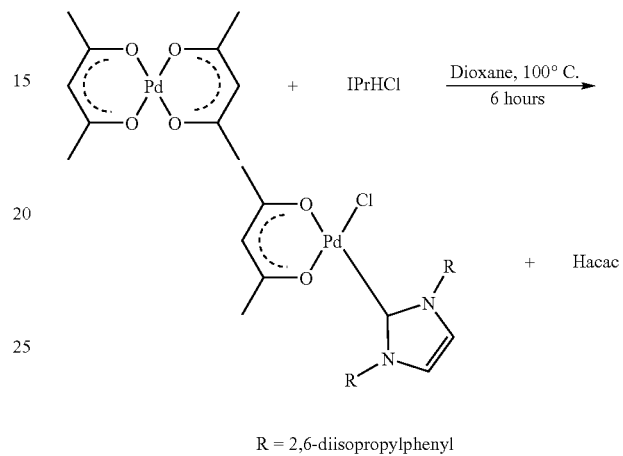

In some embodiments of the present invention, the generation of Pd Complex 2 can be achieved by the reaction path The activity of Pd Complex 2 formed with the method of Scheme 5 was evaluated for the N-aryl amination of aryl bromides and chlorides and is shown in Table 3.

TABLE 3

| N-Aryl Amination of Aryl Bromides and Chlorides | | | | |
|---|---|---|---|---|
| entry | aryl halide | amine | product | time (h) | yield (%)[b] |
| 1 | NC-⟨⟩-Br | HN⟨⟩ | NC-⟨⟩-N⟨⟩ | 2 | 90 |
| 2 | Me-⟨⟩-Br | HN⟨⟩O | Me-⟨⟩-N⟨⟩O | 0.5 | 96 |
| 3 | OMe-⟨⟩-Br | HN⟨⟩O | OMe-⟨⟩-N⟨⟩O | 4 | 96 |
| 4 | Me-⟨⟩-Br | HN(Bu)$_2$ | Me-⟨⟩-N(Bu)$_2$ | 6 | 96 |

TABLE 3-continued
N-Aryl Amination of Aryl Bromides and Chlorides
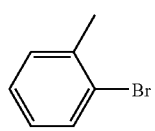
| entry | aryl halide | amine | product | time (h) | yield (%)[b] |
|---|---|---|---|---|---|
| 5 | 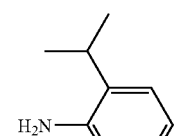 | 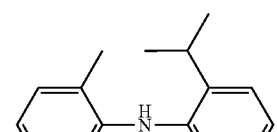 | 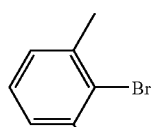 | 4 | 92 |
| 6 | 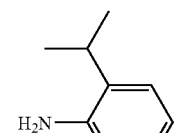 | 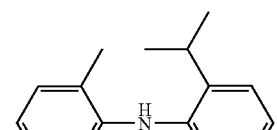 | 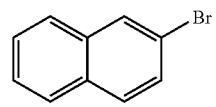 | 2 | 94 |
| 7 |  | 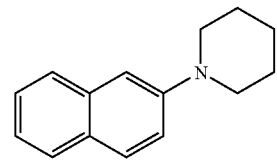 | 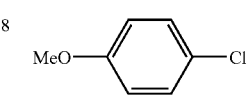 | 1.5 | 88 |
| 8 | 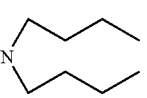 | 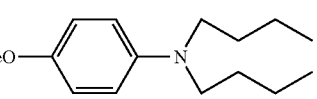 | 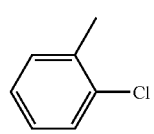 | 4 | 86 |
| 9 | 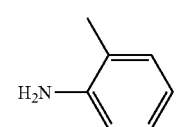 | 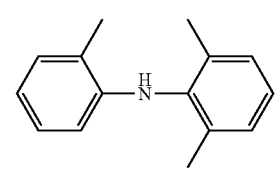 |  | 0.5 | 85 |
| 10 | 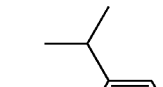 | 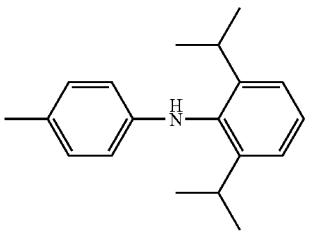 | | 6 | 97 |

TABLE 3-continued

N-Aryl Amination of Aryl Bromides and Chlorides

| entry | aryl halide | amine | product | time (h) | yield (%)[b] |
|---|---|---|---|---|---|
| 11 | o-chlorotoluene | 2,6-diisopropylaniline | N-(2,6-diisopropylphenyl)-o-toluidine | 4.5 | 89 |
| 12 | 1-chloronaphthalene | morpholine | 1-(naphthalen-1-yl)morpholine | 2 | 86 |
| 13 | 1-chloronaphthalene | N-methylaniline | N-methyl-N-(naphthalen-1-yl)aniline | 3 | 95 |

[a] Reaction conditions: aryl halide (1 mmol), amine (1.1 mmol), (IPr)Pd(acac)Cl (1 mol %), KO$^t$Bu (1.1 mmol), DME (1 mL).
[b] Isolated yields, average of two runs.

Overall, the present catalytic system displayed good efficiency toward cyclic dialkylamines with activated (entry 1), neutral (entry 2) and unactivated bromides (entry 3). In the latter entry, it is noteworthy that the combination of the unfavorable electronic effect of the methoxy group and the additional steric hinderance of such group's ortho-substitution does not lead to loss of activity. As shown by entry 4, a secondary dialkylamine, traditionally more reluctant to couple, reacted with o-bromotoluene in excellent yield.

To further challenge the tolerance of the Pd complexes of embodiments in accordance with the invention to sterically encumbered substrates, reactions with the 2, 6-diisopropylaniline were performed. Advantageously, tri- and even tetra-ortho-substituted diarylamines were obtained under mild reaction conditions (entries 5 and 6). Further, the reactivity of the less reactive aryl chlorides was examined and, as shown by entry 8, even an unactivated chloride could be coupled with a sterically hindered amine. As observed with the bromides, extremely encumbered substrates could be obtained in good yields in reasonable reaction times using chlorides (entries 9-11). Finally, the synthesis of 1- and 2-naphthylamines was investigated. Such compounds are well-known as hole transport materials or photoactive chromophores, and play an important role as a pharmacophore in a number of inhibitors. The catalytic system embodiment of the invention provided for a rapid coupling of these substrates resulting in naphthylamines being formed with good yields under mild conditions (entries 7, 12, and 13).

Heterocyclic moieties are widely represented in biologically active molecules. Therefore, heterocyclic halides and particularly heteroaromatic halides are coupling partners of great interest. Table 4 presents the results obtained with such heterocyclic aryl bromides and chlorides. The reactivity of embodiments of the present catalytic system towards N-, O- and S-containing heterocyclic halides was examined. While attempts to react O- and S-containing heterocyclic halides with several amines were not successful, N-containing heterocyclic halides were found to be suitable coupling partners. Thus, 2-Halopyridine was reacted in extremely short reaction times with secondary cyclic amines (entries 1 and 2), a secondary acyclic amine (entry 6) and aniline (entry 7). Advantageously, 3-halopyridine and quinoline, strongly unactivated when compared to 2-halopyridines, are coupled in high yields (entries 3-5 and 8). Moreover, the coupling of piperidine and 3-halopyridine was successful with similar reaction times (entries 3 and 4).

TABLE 4

N-Aryl Amination of N-Containing Heterocyclic Halides[a]

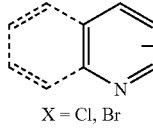

| entry | aryl halide | amine | product | time (h) | yield (%)[b] |
|---|---|---|---|---|---|
| 1 | 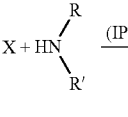 | 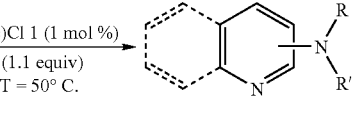 | 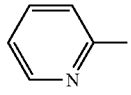 | 0.2 | 86 |
| 2 | 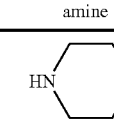 | 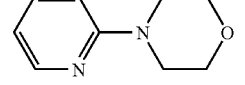 | 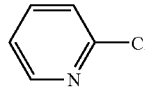 | 0.2 | 95 |
| 3 | 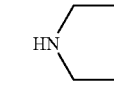 | 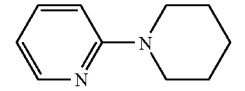 | 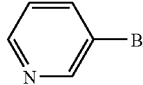 | 3.5 | 79 |
| 4 | 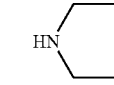 | 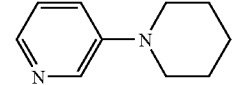 | 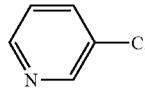 | 4 | 87 |
| 5 | 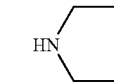 | 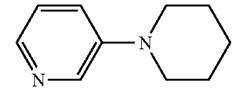 | 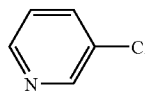 | 4 | 87 |
| 6 | 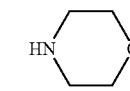 | 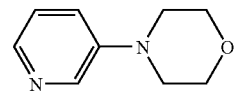 | 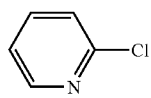 | 4 | 86 |
| 7 |  | 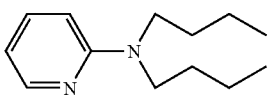 | 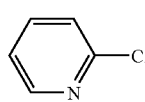 | 4 | 91 |
| 8 | 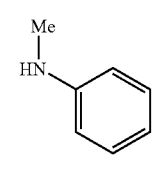 | 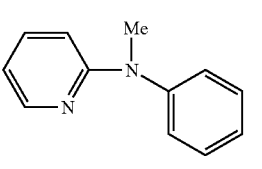 | 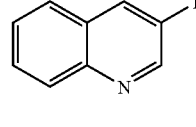 | 6 | 96 |

[a]Reaction conditions: aryl halide (1 mmol), amine (1.1 mmol), (IPr)Pd(acac)Cl 1 (1 mol %), KO$^t$Bu (1.1 mmol), DME (1 mL).
[b]Isolated yields, average of two runs.

To further investigate the reactivity profile of the Pd complex of embodiments of the present invention, the efficiency of the α-arylation of ketones was tested as only a few systems are known that can perform well using hindered aryl chlorides.

The same catalytic system embodiment of the present invention used for the N-aryl amination reactions of Table 4 was evaluated first. Employing this procedur, the reaction between chlorobenzene and propiophenone reached completion after three hours. Further optimization studies showed that in addition to the nature of the solvent and base, stoichiometry is an important factor in the course of the reaction.

Table 5 shows the results of the coupling of several ketones with different aryl halides. As shown by entries 3 and 4, neutral and activated aryl chlorides reacted rapidly with propiophenone. As expected, a less reactive ketone such as α-tetralone required more time to reach full conversion (entries 5 and 6). The coupling of sterically hindered halides such as ortho-substituted 2-chloro- and 2-bromotoluene reacted efficiently with both acetophenone (entries 1 and 2) and α-tetralone (entry 10). Advantageously, the catalytic systems of embodiments in accordance with the present invention efficiently served to activate the coupling of unactivated sterically demanding aryl chlorides with high yields realized in relatively short times (entry 7).

TABLE 5

α-Ketone Arylation Reactions of Aryl Chlorides and Bromides

| entry | aryl halide | ketone | product | time (h) | yield (%)[b] |
|---|---|---|---|---|---|
| 1 | acetophenone | 2-chlorotoluene | 1-phenyl-2-(2-tolyl)ethanone | 3.5 | 89 |
| 2 | acetophenone | 2-bromotoluene | 1-phenyl-2-(2-tolyl)ethanone | 2 | 90 |
| 3 | propiophenone | chlorobenzene | 1,2-diphenylpropan-1-one | 1 | 98 |
| 4 | propiophenone | 4-chlorobenzotrifluoride | 1-phenyl-2-(4-trifluoromethylphenyl)propan-1-one | 0.75 | 93 |
| 5 | α-tetralone | chlorobenzene | 2-phenyl-α-tetralone | 4 | 62 |
| 6 | α-tetralone | bromobenzene | 2-phenyl-α-tetralone | 3.5 | 72 |
| 7 | propiophenone | 2-chloroanisole | 1-phenyl-2-(2-methoxyphenyl)propan-1-one | 2.5 | 91 |

TABLE 5-continued

α-Ketone Arylation Reactions of Aryl Chlorides and Bromides

[Reaction scheme: R-C(=O)-CH2-R' + X-Ar-R'' → (IPr)Pd(acac)Cl 1 (1 mol %), NaOtBu, PhMe T = 60° C. → R-C(=O)-CH(R')-Ar-R''; X = Cl, Br]

| entry | aryl halide | ketone | product | time (h) | yield (%)[b] |
|---|---|---|---|---|---|
| 8 | propiophenone | 2-bromoanisole | 1-phenyl-2-(2-methoxyphenyl)propan-1-one | 1.5 | 83 |
| 9 | propiophenone | 2-bromomesitylene | 1-phenyl-2-mesitylpropan-1-one | 4.5 | 84 |
| 10 | α-tetralone | 2-bromotoluene | 2-(2-methylphenyl)-α-tetralone | 3 | 87 |
| 11 | 1-methyl-2-acetylpyrrole | 2,6-dimethylchlorobenzene | 1-(1-methylpyrrol-2-yl)-2-(2,6-dimethylphenyl)ethan-1-one | 3 | 96 |
| 12 | propiophenone | 1-chloronaphthalene | 1-phenyl-2-(1-naphthyl)propan-1-one | 2 | 96 |
| 13 | propiophenone | 2-bromonaphthalene | 1-phenyl-2-(2-naphthyl)propan-1-one | 2 | 97 |
| 14 | propiophenone | 4-bromobiphenyl | 1-phenyl-2-(4-biphenyl)propan-1-one | 1 | 95 |

[a]Reaction conditions: aryl halide (1 mmol), ketone (1.1 mmol), (IPr)Pd(acac)Cl 1 (1 mol %), NaOtBu (1.5 mmol), toluene (1 mL).
[b]Isolated yields, average of two runs.

Furthermore, compatibility of catalytic system embodiments was found with di-ortho-substituted substrates, highlighting its high tolerance for extremely hindered substrates as previously noticed in the Buchwald-Hartwig reaction. As an added advantage, a heteroaromatic ketone was α-arylated without loss of activity (Table 5, entry 11). Finally, the use of polyaromatic halides as coupling partners was examined and three propiophenones, possessing respectively the 1-naphthyl, 2-naphthyl and 4-biphenylyl moiety at the α position, were obtained in near quantitative yields (Table 5, entries 12-14). Advantageously, these products were isolated without purification by column chromatography on silica gel. Taking advantage of the low solubility of the product in alkanes, a simple pentane wash followed by a filtration was sufficient to isolate pure compounds 12, 13 and 14 which, it is believed, demonstrated the first time that such compounds were formed by a Pd-catalyzed cross-coupling reaction.

Additionally, the catalytic system embodiments of the present invention are useful for the development of synthetic strategies that utilize a functionalized norbornene monomer substrate as a synthetic synthon for obtaining other useful norbornene monomers via C—C or C—X bond formation, where the C—C bond formed is regarded as alkyl-alkyl, alkyl-aryl, and alkyl-aralkyl. Exemplary species that are useful as substrates can be selected from any one of the following monomers, D, E and F:

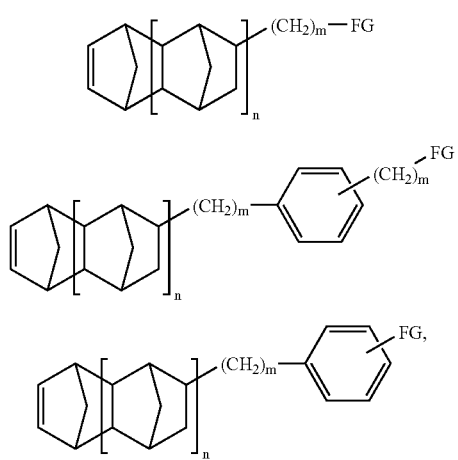

where n is selected from 0 or 1, m is selected from 0 to 5, and FG (Functional Group) is selected from Li, M(X), M(Y) or X as defined for any one of the reactions depicted in the Reaction Examples section below. In one advantageous non-limiting embodiment, FG is selected from Cl, Br, I, OTf, OMs, OTs, ZnBr, MgBr, $SiF_3$, $Si(OR)_3$, $B(OH)_2$, Bcat, 9-BBN, Bpin, ketones, aldehydes, or amines.

Exemplary organic reactions that can employ the catalytic system embodiments of the present invention can be selected from a transition metal-catalyzed or transition metal-catalyzed coupling reaction. More specifically, exemplary transition metal-catalyzed reactions are Suzuki, Suzuki-Miyaura, Murahashi, Kumada, Kumada-Corriu, Kumada-Tamao, Nozaki, Nozaki-Oshima, Negishi, Hiyama, Tamao-Kumada, Hiyama-Hatanaka, Stille, Migita-Kosugi, Buchwald-Hartwig, Murahashi, Cyanation, dehydrohalogenation, α-"Carbonyl" Arylation, Sonogashira, Cadiot-Chodkiewicz, Heck reactions, catalytic ether formation, catalytic α-arylations of ketones, dehalogenation, and catalytic throether formation reactions.

Advantageously, any of monomers D, E or F can be reacted with appropriate reagents in the presence of a catalytic system embodiment of the present invention, for example Pd(NHC)(acac)Cl, and appropriate additives to generate cross-coupled products.

Thus it is seen that embodiments of this invention provide for the synthesis of new NHC-bearing palladium complexes using $Pd(acac)_2$ as the Pd precursor. Embodiments of Pd Complex 2 display high activity for the Buchwald-Hartwig reaction and α-ketone arylation as such have short reaction times with very mild conditions.

In other embodiments, air- and moisture-stable palladium complexes of the Formulae I and II, are prepared on multigram scale in high yields, and their activity optimized for reactions based on their modular X—Y, $PR_3$, and NHC ligand motifs.

Thus, the catalyst of the invention is useful for a wide variety of reactions. Non-limiting examples of reaction schemes for which the catalyst of the invention can be used include the following reactions.

REACTION EXAMPLES

Organoborons (Suzuki-Miyaura or Suzuki Reaction)

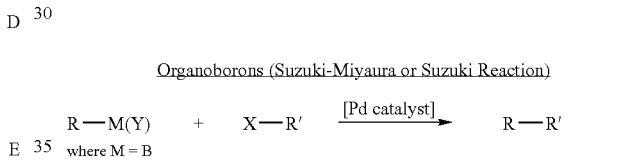
where M = B where R and R' are independently aryl, heteroaryl, alkenyl, or alkyl and R can additionally be alkynyl; Y is one of $(OH)_2$ or $(OR")_2$ where R" is $C_1$ to $C_3$ alkyl; $(O(R''')O)$ with R''' being one of $[C(CH_3)_2]_2$, $[(CH_2)—C(CH_3)_2—(CH_2)]$, ethyl, propyl or 9-BBN; $R''_3Z^*$ where R" is $C_1$ to $C_3$ alkyl and $Z^*=Li^+, Na^+$ or $K^+$; $[(OR'')_3Z^*]$ where R" and $Z^*$ are as defined above; $[(OMe)(9-BBN)Z^*]$ with $Z^*$ as defined above; or $(F_3Z^*)$ with $Z^*$ is $Li^+, Na^+, K^+$ or $(NBu_4)^+$; and X is I, Br, Cl, OTf, OTs, OMs, $OP(O)(OPh)_2$ or $N_2BF_4$.

Organolithiums (Murahashi Reaction)

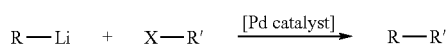

where R and R' are as defined above and X is I, Br or Cl.

Organomagnesiums (Kumada or Kumada-Corriu or Kumada-Tamao Reaction)

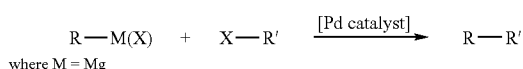
where M = Mg where R and R' are as defined above, X is I, Br, Cl, OTf, OTs, OMs or $OC(O)NZ_2$ where Z is alkyl or OAc.

Organoaluminums (Nozaki or Nozaki-Oshima or Negishi Reaction)

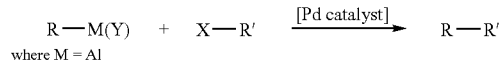
where M = Al where R is alkenyl or alkyl and R' is aryl, heteroaryl, alkenyl, alkynyl or alkyl; X is I, Br, Cl, OAc, OAlMe$_2$, OSiMe$_3$, OTf, OP(O)(OPh)$_2$ or OP(O)(OEt)$_2$; Y is (OR")$_2$ or R"$_3$Z where R" is alkyl and Z is Li$^+$, Na$^+$ or K$^+$.

Organozines (Negishi Reaction)

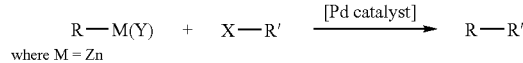
where M = Zn where R and R' are independently aryl, heteroaryl, alkenyl, alkynyl, or alkyl and R' can additionally be C(O)R''' where R''' is alkyl; X is I, Br, Cl, OTf, ONf, OTs, OAc, So$_2$Ph, or SMe; Y is I, Br, or Cl.

Organosilicons (Hiyama or Tamao-Kumada or Hiyama-Hatanaka Reaction)

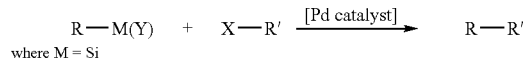
where M = Si where R and R' are independently aryl, heteroaryl, alkenyl, or alkyl and R can additionally be alkynyl; X is I, Br, Cl, OTf, ONf, or N$_2$BF$_4$; Y is one of R'''$_3$ or (OR''')$_3$ or HR'''$_2$ where R'''' is C$_1$ to C$_3$ alkyl, R$^{IV}_{3-n}$F$_n$ or R$^{IV}_{3-n}$(OH)$_n$ where R$^{IV}$ is alkyl or aryl and $0 \leq n \leq 3$, R$^V_{3-n}$(OR$^{VI}$)$_n$ where R$^V$ and R$^{VI}$ are alkyl and $0 \leq n \leq 3$, R$^{VII}_{3-n}$R$^{VIII}_n$ where R$^{VII}$ is alkyl and R$^{VIII}$ is heteroaryl and $0 \leq n \leq 3$, F$_4$Z where Z is Li$^+$, Na$^+$, K$^+$ or (NBu$_4$)$^+$, F$_5$Z$_2$ where Z is Li$^+$, Na$^+$, K$^+$ or (NBu$_4$)$^+$, (OR$^{IX}$)$_4$Z where R$^{IX}$ is alkyl and Z is Li$^+$, Na$^+$, K$^+$, or (NBu$_4$)$^+$.

Organozirconiums (Negishi Reaction)

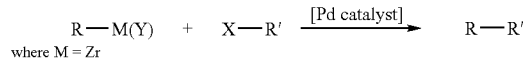
where M = Zr where R and R' are independently alkenyl and R' can additionally be aryl; X is I or Br; Y is (C$_p$)$_2$Cl.

Organotins (Stille or Migita-Kosugi Reaction)

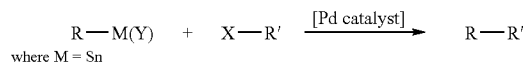
where M = Sn where R and R' are independently aryl, heteroaryl, alkenyl, alkynyl, alkyl and R' can additionally be C(O)R''' or C(N)R''' where R''' is alkyl; X is I, Br, Cl, OTf, I$^+$Ph(OTf)$^-$; Y is Me$_3$, Bu$_3$, R$^{IV}$Z$_2$ where Z is Cl and R$^{IV}$ is alkyl, or R$^V$R$^{VI}_2$ where R$^V$ is (CH$_2$)$_2$OMe and R$^{VI}$ is alkyl.

Amines (Buchwald-Hartwig Reaction)

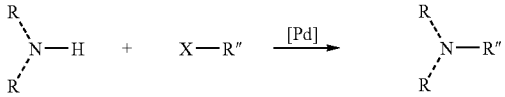

where R and R' are independent H, alkyl, alkenyl, aryl, or heteroaryl (with N being intracyclic, pyrroles, indoles, or carbazoles), C(O)R''' where R''' is H, alkyl, or aryl, CO$_2$R$^{IV}$ where R$^{IV}$ is alkyl, C(O)NR$^V_2$ where R$^V$ is H, alkyl, or aryl, SO$^2$R$^{VI}$ where R$^{VI}$ is aryl, S(O)R$^{VII}_2$ where RVII is alkyl or aryl, =CPh$_2$, N=CPh$_2$, SiPh$_3$ or Li; R" is aryl, heteroaryl, alkenyl, or alkyl (if X is OH); X is I Br, Cl, OH (only if R" is alkyl), OTf, ONf, OTs, OR OSO$_2$Ph.

Alcohols (Buchwald-Hartwig Reaction)

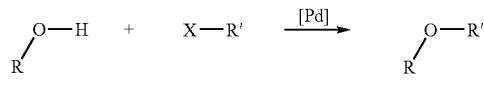

where R is alkyl, aryl, alkenyl, or SiR where R is alkyl (for the above alcohols, the corresponding alkoxide salts (Li, Na, K) can be employed); R' is aryl or heteroaryl; X is Br of Cl.

Thiols (Murahashi Reaction)

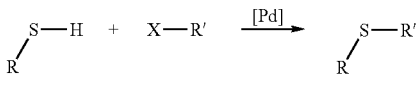

where R and R' are independently aryl and R can additionally be alkyl and Si(iPr)$_3$; X is I, Br, Cl, OTf, or OTs.

Cyanation

where [CN] is KCN, NaCN, Zn(CN)$_2$, (CH$_3$)$_2$C(OH)(CN), Me$_3$Si(CN), or K$_4$[Fe(CN)$_6$]; X is I; Br, Cl, or OTf; R is aryl or heteroaryl.

Dehalogenation

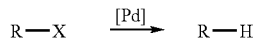

where R is aryl or heteroaryl; X is I, Br, or Cl

α-"Carbonyl" Arylation

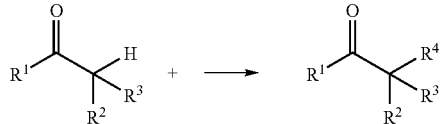

-continued

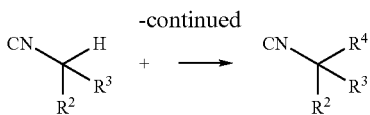

where $R^1$ is alkyl, aryl, heteroaryl, $OR^5$ where $R^5$ is alkyl, $NR^6{}_2$ where $R^6$ is alkyl or aryl; $R^{2,3}$ is H, F, alkyl, N is $CPh_2$, aryl, $CO_2R^7$ where $R^7$ is alkyl; X is I, Br, Cl, or OTf; $R^4$ is aryl, heteroaryl, or alkenyl.

Alkynes (Sonogashira Reaction) [when R'' = alkynyl, called Cadiot-Chodkiewicz Reaction]

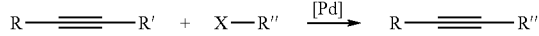

where R is aryl, heteroaryl, alkenyl, alkynyl, alkyl, $SiR'''_3$ where R''' is alkyl, O(alkyl), $SiR''R^V{}_2$ where R''' is alkyl and $R^V$ is aryl, or where $R^{IV}$ is OH and $R^V$ is alkyl; R' is H, $SiR^{VI}{}_3$ where $R^{VI}$ is alkyl; X is I, Br, Cl, or OTf; R'' is aryl, heteroaryl, alkenyl, alkynyl, alkyl, or C(O) $R^{VII}$ where $R^{VII}$ is alkyl.

Alkenes (Heck Reaction)

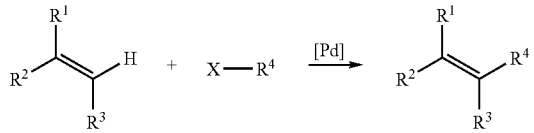

where $R^{1,2,3}$ is H, F, heteroaryl, alkenyl, alkynyl, alkyl, C(O) $R^5$ where $R^5$ is H, alkyl, aryl, heteroaryl; $S(O)R^6$ where $R^6$ is alkyl, aryl, heteroaryl; $CO_2R^7$ where $R^7$ is H, alkyl, aryl, heteroaryl; CN; $OR^8$ where $R^8$ is alkyl, aryl; $SR^9$ where Z is alkyl or aryl; $SiR^{10}{}_3$ where $R^{10}$ is alkyl or aryl; $SnR^{11}{}_3$ where $R^{11}$ is alkyl or aryl; $NR^{12}{}_2$ where $R^{12}$ is H, alkyl, aryl or heteroaryl; $NO_2$; $PR^{13}{}_2$ where $R^{13}$ is alkyl or aryl; $P(O)R^{14}{}_2$ where $R^{14}$ is alkyl or aryl; X is I, Br, Cl, C(O)Cl, $CO_2(CO)R^{15}$ where $R^{15}$ is alkyl; $CO_2R^{16}$ where $R^{16}$ is H or aryl; OTf; ONf; OTs; $SO_2Cl$; $OP(O)(OPh)_2$; $OP(O)(OEt)_2$; $N_2BF_4$; $BiPh_3{}^+B_4{}^-$; or $I^+Ph$ $(Z)^-$ where Z is OTf, $BF_4$; $R^4$ is aryl, heteroaryl, or alkenyl Experimental Details $^1$H and $^{13}$C nuclear magnetic resonance spectra were recorded on a Varian-300 or Varian-400 MHz spectrometer at ambient temperature in $CDCl_3$ (Cambridge Isotope Laboratories, Inc), unless otherwise noted. Elemental analyses were performed at Robertson Microlit Laboratories, Inc., Madison, N.J. IPr.HCl was synthesized according to literature procedures.

Example 1

Synthesis of (IPr)Pd(acac)$_2$ (Pd Complex 1)

In a glove box, a Schlenk flask equipped with a magnetic bar was loaded with free carbene IPr (855 mg, 2.2 mmol), Pd(acac)$_2$ (609 mg, 2 mmol) and dry toluene (30 mL), and sealed with a rubber cap. The mixture was stirred at room temperature for two hours. The solvent was evaporated in vacuo and THF (25 mL) was added. The solution was filtered and the solid washed with THF (2×5 mL). The solvent was evaporated in vacuo; the complex was then triturated with cold pentane (25 mL) and filtered out the solution. Recrystallization in a chloroform/pentane mixture (25/75) yielded 1.28 g (93%) of the desired compound. $^1$H-NMR (400 MHz, $C_6D_6$): δ 7.28-7.24 (m, 2H), 7.18 (d, J=8.0 Hz, 4H), 6.47 (s, 2H), 5.90 (s, 1H), 4.78 (s, 1H), 2.88 (q, J=6.8 Hz, 4H), 2.63 (d, J=0.8 Hz, 3H), 2.01 (d, J=0.8 Hz, 3H), 1.63 (s, 3H), 1.35 (d, J=6.8, 12H), 1.31 (s, 3H), 0.97 (d, J=6.8, 12H). $^{13}$C-NMR (100 MHz, $C_6D_6$): 207.5, 192.9, 188.1, 185.6, 183.3, 161.2, 146.9, 135.9, 131.2, 130.4, 125.7, 125.2, 124.7, 124.5, 104.8, 100.3, 47.2, 31.9, 31.5, 29.3, 29.0, 28.9, 28.1, 27.0, 26.5, 26.2, 25.1, 24.0, 23.8, 23.4. Elemental Analysis: Anal. Calcd.: C, 64.11; H, 7.27; N, 4.04. Found: C, 63.89; H, 7.06; N: 3.86.

Example 2

One-Pot Synthesis of (IPr)Pd(acac)Cl (Pd Complex 2)

In a glove box, a Schlenk flask equipped with a magnetic bar was loaded with the free carbene IPr (2.73 g, 7 mmol), Pd(acac)$_2$ (1.53 g, 5 mmol) and dry dioxane (50 mL), and sealed with a rubber cap. The mixture was stirred at room temperature for two hours. After that time, 1.25 mL of HCl 4M in dioxane was injected in the solution and the mixture was stirred at room temperature for another 2 hours. The solvent was then evaporated in vacuo and diethyl ether was added until no more solid dissolved (20 mL). The solution was filtered and the solid washed with diethyl ether (2×10 mL). The solvent was evaporated in vacuo and the powder obtained kept under vacuum overnight to yield 2.85 g (90%) of the desired product. $^1$H-NMR (400 MHz, $CDCl_3$): δ 7.51 (t, J=7.6 Hz, 2H), 7.35 (d, J=8 Hz, 4H), 7.12 (s, 2H), 5.12 (s, 1H), 2.95 (q, J=6.4 Hz, 4H), 1.84 (s, 3H), 1.82 (s, 3H), 1.34 (d, J=6.4 Hz, 12H), 1.10 (d, J=6.4 Hz, 12H). $^{13}$C-NMR (100 MHz, $CDCl_3$): 187.1, 184.1, 156.4, 147.0, 135.5, 134.8, 130.9, 125.7, 124.7, 124.6, 99.9, 29.1, 30.0, 27.6, 26.8, 23.7, 23.5. Elemental Analysis: Anal. Calcd.: C, 61.05; H, 6.88; N, 4.45. Found: C, 60.78; H, 7.15; N: 4.29.

Example 3

One-Pot Synthesis of (IPr)Pd(acac)Cl (Pd Complex 2)

In a glove box, a Schlenk flask equipped with a magnetic bar is loaded with the imidazolium salt IPr HCl (2.96 g, 7 mmol), Pd(acac)$_2$ (1.53 g, 5 mmol) and dry dioxane (100 mL). The flask was taken outside the glove box and placed in an oil bath at 100° C. over a magnetic stirrer for 6 hours. After that time, the solution looked clear with no solid remaining. The solvent was evaporated in vacuo and diethyl ether was added until no more solid was dissolved. The solution is filtered and the solid washed with diethyl ether (2×10 mL). The solvent was evaporated in vacuo to yield 2.99 g (95%) of the desired compound as a yellow powder.

$^1$H NMR (5, 400 MHz, $CDCl_3$): 7.51 (t, J=7.8 Hz, 2H), 7.35 (d, J=7.8 Hz, 4H), 7.12 (s, 2H), 5.12 (s, 1H), 2.95 (q, J=6.4 Hz, 4H), 1.84 (s, 3H), 1.82 (s, 3H), 1.34 (d, J=6.4 Hz, 12H), 1.10 (d, J=6.4 Hz, 12H).

$^{13}$C NMR (δ, 100 MHz, $CDCl_3$): 187.1, 184.1, 156.4, 147.0, 135.5, 134.8, 130.9, 125.7, 124.7, 124.6, 99.9, 29.1, 30.0, 27.6, 26.8, 23.7, 23.5.

Anal. Calcd. for $C_{32}H_{43}ClN_2O_2Pd$ (MW 629.57): C, 61.05; H, 6.88; N, 4.45. Found: C, 60.78; H, 7.15; N: 4.29.

Examples 4-9

Cross-Coupling Reactions: Buchwald-Hartwig Reaction of Aryl Chlorides with Primary and Secondary Amines In each of Examples 6-11, the following procedure was used where the specific amine and aryl chloride employed, and product formed for such examples is found in Table 1, as indicated.

In a glove box, 2 (1 mol %, 6 mg) potassium tert-butoxide (1.1 mmol, 124 mg) and DME (1 mL) were added in turn to a vial equipped with a magnetic bar, and sealed with a screw cap fitted with a septum. Outside the glove box, the amine (1.1 mmol) and the aryl chloride (1 mmol) were injected in turn through the septum. The vial was then placed in an oil bath at 50° C. and the mixture stirred on a stirring plate. The reaction was monitored by gas chromatography. When the reaction reached completion, or no further conversion could be observed, the vial was allowed to cool down to room temperature. Water was added to the reaction mixture; the organic layer was extracted with diethyl ether and dried over magnesium sulfate. The solvent was then evaporated in vacuo. When necessary the product was purified by flash chromatography on silica gel (pentane/ethyl acetate: 9/1). Reported yields are the average of two runs.

Example 4

4-(4-Methylphenyl)morpholine (Table 1, Entry 1)

The procedure afforded 171 mg (97%) of the title compound.

Example 5

4-(2-Pyridinyl)morpholine (Table 1, Entry 2)

The procedure afforded 160 mg (98%) of the title compound

Example 6

4-(2,6-Dimethylphenyl)morpholine (Table 1, Entry 3)

The procedure afforded 170 mg (90%) of the title compound

Example 7

4-(4-Methoxyphenyl)morpholine (Table 1, Entry 4)

The procedure afforded 190 mg (99%) of the title compound

Example 8

N,N-Dibutyl-p-toluidine (Table 1, Entry 5)

The procedure afforded 207 mg (95%) of the title compound

Example 9

N-Phenyl-N-(pyridin-2-yl)pyridin-2-amine (Table 1, Entry 6)

The procedure with 2-chloropyridine (2.1 mmol, 197 μL), aniline (1 mmol, 93 μL) KO$^t$Bu (2.2 mmol, 248 mg), (IPr)Pd(acac)Cl (1 mol %, 12.6 mg) and DME (2 mL) afforded 230 mg (93%) of the title compound. $^1$H NMR (400 Mhz, (CD$_3$)$_2$CO): δ 8.22 (d, J=4 Hz, 2H), 7.61 (m, 2H), 7.38 (t, J=8.1 Hz, 2H), 7.24-7.16 (m, 3H), 7.00 (d, J=8.4 Hz, 2H), 6.97-6.94 (m, 2H). $^{13}$C NMR (100 MHz, ((CD$_3$)$_2$CO): 159.5 (C), 149.4 (CH), 146.6(C), 138.6 (CH), 130.7 (CH), 128.9 (CH), 126.6 (CH), 119.3 (CH), 118.0 (CH). Elemental Analysis: Anal. Calcd. for C$_{16}$H$_{13}$N$_3$ (MW 247.29): C, 77.71; H, 5.30; N, 16.99. Found: C, 77.79; H, 5.57; N, 16.93.

Examples 10-15

α-Ketone Arylation of Alkyl or Aryl Ketones

In each of Examples 12-17, the following procedure was used where the specific ketone and aryl chloride employed, and product formed for such examples is found in Table 2, as indicated.

In a glove box, 2 (1 mol %, 6 mg) sodium tert-butoxide (1.5 mmol, 144 mg) and toluene (1 mL) were added in turn to a vial equipped with a magnetic bar, and sealed with a screw cap fitted with a septum. Outside the glove box, the ketone (1.1 mmol) and the aryl chloride (1 mmol) were injected in turn through the septum. The vial was then placed in an oil bath at 60° C. and the mixture stirred on a stirring plate. The reaction was monitored by gas chromatography. When reaction reached completion, or no further conversion could be observed, the vial was allowed to cool down to room temperature. Water was added to the reaction mixture; the organic layer was extracted with diethyl ether and dried over magnesium sulfate. The solvent was then evaporated in vacuo. When necessary the product was purified by flash chromatography on silica gel (pentane/ethyl acetate: 9/1). The reported yields are the average of two runs.

Example 10

2-(4-Methylphenyl)-1-phenyl-1-propanone (Table 2, Entry 1)

The procedure afforded 216 mg (97%) of the title compound

Example 11

1-(Naphthyl)-2-phenylethanone (Table 2, Entry 2)

The procedure afforded 173 mg (70%) of the title compound

Example 12

α-Phenylcyclohexanone (Table 2, Entry 3)

The procedure afforded 150 mg (86%) of the title compound

Example 13

2-(2,6-Dimethylphenyl)-1-phenylethanone (Table 2, Entry 4)

The procedure afforded 212 mg (95%) of the title compound. $^1$H NMR (400 MHz, CD$_2$Cl$_2$): δ 8.09 (d, J=7.2 Hz, 2H), 7.64 (t, J=7.2 Hz, 1H), 7.54 (t, J=8.0 Hz, 2H), 7.14-7.06 (m, 3H), 4.40 (s, 2H), 2.21 (s, 6H). $^{13}$C NMR (100 MHz, CD$_2$Cl$_2$): 197.5 (C), 137.7 (C), 133.7 (CH), 133.4 (C), 129.2 (CH), 128.5 (CH), 128.3 (CH), 127.3 (CH), 114.0 (C), 40.2 (CH$_2$), 20.6 (CH$_3$). Elemental Analysis: Anal. Calcd. for C$_{16}$H$_{16}$O (MW 224.30): C, 85.68; H, 7.19. Found: C, 85.36; H, 7.23.

Example 14

2-(p-Methoxyphenyl)-acetophenone (Table 2, Entry 5)

The procedure afforded 208 mg (92%) of the title compound

Example 15

1-Phenyl-2-(3-pyridinyl)-1-propanone (Table 2, Entry 6)

The procedure afforded 188 mg (89%) of the title compound.

Examples 16-28

Table 3

Synthesis of (IPr)Pd(acac)Cl (1): The catalyst was prepared in the same manner as described with respect to Example 3.

Buchwald-Hartwig Cross-Coupling of Aryl Halides with Primary and Secondary Amines.

General procedure: In a glove box, (IPr)Pd(acac)Cl (0.01 mmol, 6.3 mg), potassium tert-butoxide (1.1 mmol, 124 mg) and anhydrous dimethoxyethane (DME) (1 mL) were added in turn to a vial equipped with a magnetic bar, and sealed with a screw cap fitted with a septum. Outside the glove box, the amine (1.1 mmol) and the aryl halide (1 mmol) were injected in turn through the septum. If one of the two starting materials was a solid, it was added to the vial inside the glove box and DME and the second starting material were added outside the glove box under argon. The reaction mixture was then stirred at room temperature unless otherwise indicated. When the reaction reached completion, or no further conversion could be observed by Gas Chromatography (GC), water was added to the reaction mixture, the organic layer was extracted with tert-butylmethyl ether (MTBE), dried over magnesium sulfate and the solvent was evaporated in vacuo. When necessary the product was purified by flash chromatography on silica gel. The reported yields are the average of at least two runs.

Example 16

N-4-(Cyanophenyl)piperidine (Table 3, Entry 1)

The above general procedure yielded, after flash chromatography on silica gel (pentane/MTBE, 95/5), 168 mg (90%) of the title compound.

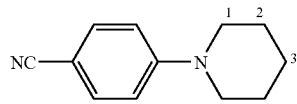

$^1$H NMR (400 MHz, CDCl$_3$): δ 7.42 (d, J=9.0 Hz, 2H, H$^{Ar}$), 6.82 (d, J=9.0 Hz, 2H, H$^{Ar}$), 3.31 (t, J=5.1 Hz, 4H, H$^1$), 1.64 (s broad, 6H, H$^2$+H$^3$).

$^{13}$C NMR (100 MHz, CDCl$_3$): δ 153.5 (C, C—CN), 133.3 (CH, C$^{Ar}$), 120.3 (C, C—N), 114.0 (CH, C$^{Ar}$), 98.7 (C, CN), 48.3 (CH$_2$, C$^1$), 25.2 (CH$_2$, C$^2$), 24.2 (CH$_2$, C$^3$).

Example 17

N-(o-Tolyl)morpholine (Table 3, Entry 2)

The above general procedure yielded, after flash chromatography on silica gel (pentane/MTBE, 90/10), 170 mg (96%) of the title compound.

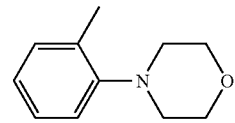

$^1$H NMR (300 MHz, CDCl$_3$): δ 7.20-7.15 (m, 2H, H$^{Ar}$), 7.03-6.97 (m, 2H$^{Ar}$), 3.84 (t, J=4.6 Hz, O—CH$_2$), 2.90 (t, J=4.6 Hz, 6H, N—CH$_2$), 2.31 (s, 3H, CH$_3$).

$^{13}$C NMR (75 MHz, CDCl$_3$): δ 151.5 (C, C$^{Ar}$), 132.8 (CH, C$^{Ar}$), 131.3 (CH, C$^{Ar}$), 126.8 (CH, C$^{Ar}$), 123.6 (CH, C$^{Ar}$), 119.2 (CH, C$^{Ar}$), 67.5 (CH$_2$, O—CH$_2$), 52.5 (CH$_2$, N—CH$_2$), 18.0 (CH$_3$, CH$_3$).

Example 18

N-(2-Methoxyphenyl)morpholine (Table 3, Entry 3)

The above general procedure yielded, after flash chromatography on silica gel (pentane/MTBE, 90/10), 186 mg (96%) of the title compound.

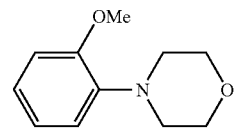

$^1$H NMR (300 MHz, CDCl$_3$): δ 7.00-6.95 (m, 2H, H$^{Ar}$), 6.89 (d, J=6.6 Hz, 1H, H$^{Ar}$), 6.83 (d, J=7.5 Hz, 1H, H$^{Ar}$), 3.85 (t, J=4.5 Hz, 2H, O—CH$_2$), 3.81 (s, 3H, OMe), 3.03 (t, J=4.5 Hz, 2H, N—CH$_2$).

$^{13}$C NMR (75 MHz, CDCl$_3$): δ 152.1 (C, C$^{Ar}$—O), 141.0 (C, C$^{Ar}$—N), 123.0 (CH, C$^{Ar}$), 120.9 (CH, C$^{Ar}$), 117.9 (CH, C$^{Ar}$), 111.2 (CH, C$^{Ar}$), 67.1 (CH$_3$, OMe), 55.2 (CH$_2$, O—CH$_2$), 51.0 (CH$_2$, N—CH$_2$).

Example 19

N,N-Dibutyl-N-(o-tolyl)amine (Table 3, Entry 4)

The above general procedure yielded, after flash chromatography on silica gel (pentane/DCM, 90/10), 210 mg (96%) of the title compound.

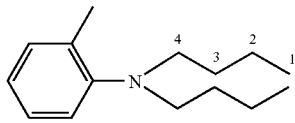

$^1$H NMR (300 MHz, CDCl$_3$): δ 7.17-7.12 (m, 2H, H$^{Ar}$), 6.62-6.56 (m, 2H, H$^{Ar}$), 3.20 (t, J=7.8 Hz, 4H, H$^4$), 2.19 (s, 3H, C$^{Ar}$—CH$_3$), 1.56-1.48 (m, 4H, H$^3$), 1.35-1.27 (m, 4H$^2$), 0.92 (t, J=7.5 Hz, 6H, H$^1$).
$^{13}$C NMR (75 MHz, CDCl$_3$): δ 148.3 (C, C$^{Ar}$), 131.9 (C, C$^{Ar}$), 129.2 (CH, C$^{Ar}$), 115.3 (CH, C$^{Ar}$), 111.9 (CH, C$^{Ar}$), 50.9 (CH$_2$, C$^4$), 29.6 (CH$_2$, C$^3$), 20.4 (CH$_2$, C$^2$), 16.7 (CH$_3$, C$^{Ar}$—CH$_3$), 14.0 (CH$_3$, C$^1$).

Example 20

N-(2,6-Diisopropylphenyl)-N-(o-tolyl)amine (Table 3, Entry 5)

The above general procedure yielded, after flash chromatography on silica gel (pentane/DCM, 90/10), 246 mg (92%) of the title compound.

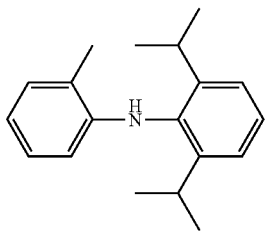

$^1$H NMR (300 MHz, CDCl$_3$): δ 7.27-7.20 (m, 3H, H$^{Ar}$), 7.07 (d, J=7.2 Hz, 1H, H$^{Ar}$), 6.91 (t, J=7.5 Hz, 1H, H$^{Ar}$), 6.63 (t, J=6.0 Hz, 1H, H$^{Ar}$), 6.12 (d, J=8.4 Hz, 1H, H$^{Ar}$), 3.12 (septet, J=6.5 Hz, 2H, CH(CH$_3$)$_2$), 2.30 (s, 3H, C$^{Ar}$—CH,), 1.16 (d, J=6.5 Hz, 6H, CH(CH$_3$)$_2$), 1.10 (d, J=6.5 Hz, 6H, CH(CH$_3$)$_2$).
$^{13}$C NMR (75 MHz, CDCl$_3$): δ 147.3 (C, C$^{Ar}$—N), 146.2 (C, C$^{Ar}$—N), 135.9 (C, C$^{Ar}$), 130.3 (CH, C$^{Ar}$), 127.2 (CH, C$^{Ar}$), 127.1 (CH, C$^{Ar}$), 123.9 (CH, C$^{Ar}$), 121.3 (C, C$^{Ar}$), 117.7 (CH, C$^{Ar}$), 111.6 (CH, C$^{Ar}$), 28.4 (CH, CH(CH$_3$)$_2$), 24.8 (CH$_3$, CH(CH$_3$)$_2$), 23.2 (CH$_3$, CH(CH$_3$)$_2$), 17.7 (CH$_3$, C$^{Ar}$—CH$_3$).

Example 21

N-(2,6-Diisopropylphenyl)-N-(2,6-dimethylphenyl)amine (Table 3, Entry 6)

The above general procedure yielded, after flash chromatography on silica gel (pentane/DCM, 90/10), 264 mg (94%) of the title compound.

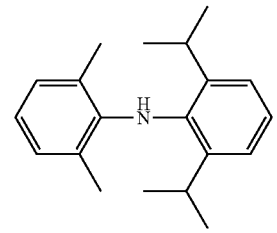

$^1$H NMR (300 MHz, CDCl$_3$): δ 7.13-7.09 (m, 3H, H$^{Ar}$), 6.91 (d, J=7.5 Hz, 2H, H$^{Ar}$), 6.69 (t, J=7.5 Hz, 1H, H$^{Ar}$), 3.15 (septet, J=6.6 Hz, 2H, CH(CH$_3$)$_2$), 1.97 (s, 6H, C$^{Ar}$—CH$_3$), 1.11 (d, J=6.6 Hz, 12H, CH(CH$_3$)$_2$).
$^{13}$C NMR (75 MHz, CDCl$_3$): δ 144.3 (C, C$^{Ar}$), 143.3 (C, C$^{Ar}$), 139.0 (C, C$^{Ar}$), 129.7 (CH, C$^{Ar}$), 125.8 (C, C$^{Ar}$), 125.0 (CH, C$^{Ar}$), 123.4 (CH, C$^{Ar}$), 119.8 (CH, C$^{Ar}$), 28.2 (CH, CH(CH$_3$)$_2$), 23.7 (CH$_3$, CH(CH$_3$)$_2$), 19.5 (CH$_3$, C$^{Ar}$—CH$_3$).

Example 22

N-(2-Naphthyl)piperidine (Table 3, Entry 7)

The above general procedure yielded, after flash chromatography on silica gel (pentane/DCM, 95/5), 186 mg (88%) of the title compound.

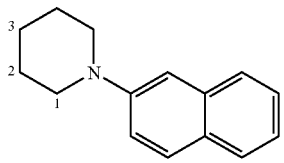

$^1$H NMR (400 MHz, CDCl$_3$): δ 7.69-7.65 (m, 3H, H$^{Ar}$), 7.39-7.35 (m, 1H, H$^{Ar}$), 7.28-7.23 (m, 2H, H$^{Ar}$), 7.11 (s, 1H, H$^{Ar}$), 3.23 (t, J=4.8 Hz, 4H, H$^1$), 1.77-1.71 (m, 4H, H$^2$), 1.62-1.58 (m, 2H, H$^3$).
$^{13}$C NMR (100 MHz, CDCl$_3$): δ 150.3 (C, N—C$^{Ar}$), 134.9 (C, C$^{Ar}$), 128.7 (CH, C$^{Ar}$), 128.5 (C, C$^{Ar}$), 127.6 (CH, C$^{Ar}$), 126.9 (CH, C$^{Ar}$), 126.3 (CH, C$^{Ar}$), 123.3 (CH, C$^{Ar}$), 120.4 (CH, C$^{Ar}$), 110.5 (CH, C$^{Ar}$), 51.2 (CH$_2$, C$^1$), 26.1 (CH$_2$, C$^2$), 24.6 (CH$_2$, C$^3$).

Example 23

N,N-Dibutyl-N-(4-methoxyphenyl)amine (Table 3, Entry 8)

The above general procedure yielded, after flash chromatography on silica gel (pentane/MTBE, 95/5), 219 mg (93%) of the title compound.

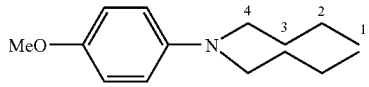

$^1$H NMR (300 MHz, CDCl$_3$): δ 6.80 (d, J 2.1 Hz, 2H, H$^{Ar}$), 6.63 (d, J=2.1 Hz, 2H, H$^{Ar}$), 3.72 (s, 3H, O—CH$_3$), 3.16 (t, J=7.8 Hz, 4H, H$^4$), 1.56-1.46 (m, 4H, H$^3$), 1.38-1.26 (m, 4H, H$^2$), 0.93 (t, J=7.5 Hz, 6H, H$^1$).

$^{13}$C NMR (75 MHz, CDCl$_3$): δ 151.3 (C, C$^{ar}$—O), 143.5 (C, C$^{Ar}$—N), 114.9 (CH, C$^{Ar}$), 114.7 (CH, C$^{Ar}$), 55.9 (CH$_3$, O—CH$_3$), 51.8 (CH$_2$, C$^4$), 29.7 (CH$_2$, C$^3$), 20.6 (CH$_2$, C$^2$), 14.1 (CH$_3$, C$^1$).

Example 24

N-(2,6-Dimethylphenyl)-N-(o-tolyl)amine (Table 3, Entry 9)

The above general procedure yielded, after flash chromatography on silica gel (pentane/MTBE, 95/5), 180 mg (85%) of the title compound.

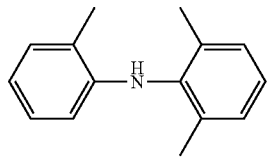

$^1$H NMR (300 MHz, CDCl$_3$): δ 7.15-7.09 (m, 4H, H$^{Ar}$), 6.99-6.96 (m, 1H, H$^{Ar}$), 6.72 (t, J=4.8 Hz, 1H, H$^{Ar}$), 6.19 (d, J=6.0 Hz, 1H, H$^{Ar}$), 2.32 (s, 3H, C$^{Ar}$—CH$_3$), 2.20 (s, 6H, C$^{Ar}$—CH$_3$).

$^{13}$C NMR (75 MHz, CDCl$_3$): δ 144.3 (C, C$^{Ar}$), 139.9 (C, C$^{Ar}$), 135.7 (C, C$^{Ar}$), 130.4 (CH, C$^{Ar}$), 128.7 (CH, C$^{Ar}$), 127.0 (CH, C$^{Ar}$), 125.7 (CH, C$^{Ar}$), 122.4 (C, C$^{Ar}$), 118.2 (CH, C$^{Ar}$), 111.8 (CH, C$^{Ar}$), 18.3 (CH$_3$, C$^{Ar}$—CH$_3$), 17.7 (CH$_3$, C$^{Ar}$—CH$_3$).

Example 25

N-(2,6-Diisopropylphenyl)-N-p-tolyl)amine (Table 3, Entry 10)

The above general procedure yielded, after flash chromatography on silica gel (pentane/DCM, 90/10), 259 mg (97%) of the title compound.

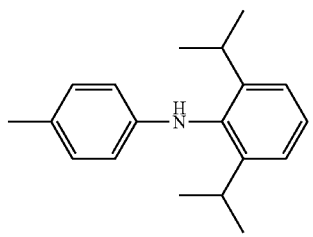

$^1$H NMR (300 MHz, CDCl$_3$): δ 7.26-7.18 (m, 3H, H$^{Ar}$), 7.93 (d, J=6.0 Hz, 2H, H$^{Ar}$), 6.39 (d, J=8.4 Hz, 2H, H$^{Ar}$), 3.19 (septet, J=6.3 Hz, 2H, CH(CH$_3$)$_2$), 2.22 (s, 3H, CH$_3$), 1.13 (d, J=6.3 Hz, 12H, CH(CH$_3$)$_2$).

$^{13}$C NMR (75 MHz, CDCl$_3$): δ 147.5 (C, C$^{Ar}$—N), 146.0 (C, C$^{Ar}$—N), 135.7 (C, C$^{Ar}$), 129.9 (CH, C$^{Ar}$), 127.17 (C, C$^{Ar}$), 126.99 (C, C$^{Ar}$), 123.9 (CH, C$^{Ar}$), 113.2 (CH, C$^{Ar}$), 28.4 (CH, CH(CH$_3$)$_2$), 24.0 (CH$_3$, CH(CH$_3$)$_2$), 20.6 (CH$_3$, CH$_3$—C$^{Ar}$).

Example 26

N-(2,6-Diisopropylphenyl)-N-(o-tolyl)amine (Table 3, Entry 11)

The above general procedure yielded, after flash chromatography on silica gel (pentane/DCM, 90/10), 237 mg (89%) of the title compound.

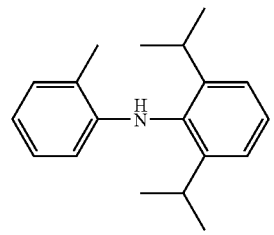

$^1$H NMR (300 MHz, CDCl$_3$): δ 7.27-7.20 (m, 3H, H$^{Ar}$), 7.07 (d, J=7.2 Hz, 1H, H$^{Ar}$), 6.91 (t, J=7.5 Hz, 1H, H$^{Ar}$), 6.63 (t, J=6.0 Hz, 1H, H$^{Ar}$), 6.12 (d, J=8.4 Hz, 1H, H$^{Ar}$), 3.12 (septet, J=6.5 Hz, 2H, CH(CH$_3$)$_2$), 2.30 (s, 3H, C$^{Ar}$—CH$_3$), 1.16 (d, J=6.5 Hz, 6H, CH(CH$_3$)$_2$), 1.10 (d, J=6.5 Hz, 6H, CH(CH$_3$)$_2$).

$^{13}$C NMR (75 MHz, CDCl$_3$): δ 147.3 (C, C$^{Ar}$—N), 146.2 (C, C$^{Ar}$—N), 135.9 (C, C$^{Ar}$), 130.3 (CH, C$^{Ar}$), 127.2 (CH, C$^{Ar}$), 127.1 (CH, C$^{Ar}$), 123.9 (CH, C$^{Ar}$), 121.3 (C, C$^{Ar}$), 117.7 (CH, C$^{Ar}$), 111.6 (CH, C$^{Ar}$), 28.4 (CH, CH(CH$_3$)$_2$), 24.8 (CH$_3$, CH(CH$_3$)$_2$), 23.2 (CH$_3$, CH(CM$_3$)$_2$), 17.7 (CH$_3$, C$^{Ar}$—CH$_3$).

Example 27

N-(1-Naphthyl)morpholine (Table 3, Entry 12)

The above general procedure yielded, after flash chromatography on silica gel (pentane/DCM, 90/10), 183 mg (86%) of the title compound.

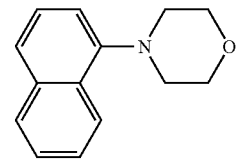

$^1$H NMR (δ, 300 MHz, CDCl$_3$): 8.19-8.16 (m, 1H, H$^{Ar}$), 7.78-7.75 (m, 1H, H$^{Ar}$), 7.52-7.31 (m, 4H, H$^{Ar}$), 6.98 (d, J=7.2 Hz, 1H, H$^{Ar}$), 3.89 (t, J 4.5 Hz, 4H, OCH$_2$), 3.00 (t, J=4.5 Hz, 4H, NCH$_2$).

$^{13}$C NMR (δ, 75 MHz, CDCl3): 149.5 (C, C$^{Ar}$), 134.9 (C, C$^{Ar}$), 128.9(C, C$^{Ar}$), 128.5 (CH, C$^{Ar}$), 125.93 (CH, C$^{Ar}$), 125.88 (CH, C$^{Ar}$), 125.5 (CH, C$^{Ar}$), 123.8 (CH, C$^{Ar}$), 123.5 (CH, C$^{Ar}$), 114.7 (CH, C$^{Ar}$), 67.5 (CH$_2$, OCH$_2$), 53.5 (CH$_2$, NCH$_2$).

Example 28

N-Methyl-N-(1-naphthyl)phenylamine (Table 3, Entry 13)

The above general procedure yielded, after flash chromatography on silica gel (pentane/DCM, 95/5), 222 mg (95%) of the title compound.

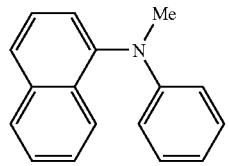

$^1$H NMR (δ, 300 MHz, CDCl$_3$): 7.86-7.80 (m, 2H, H$^{Ar}$), 7.69 (d, J=8.4 Hz, 1H, H$^{Ar}$), 7.42-7.27 (m, 4H, H$^{Ar}$), 7.12-7.07 (m, 2H, H$^{Ar}$), 6.68 (t, J=7.2 Hz, 1H, H$^{Ar}$), 6.58 (d, J=7.8 Hz, 2H, H$^{Ar}$), 3.30 (s, 3H, Me).

$^{13}$C NMR (δ, 75 MHz, CDCl3): 150.3 (C, N—C$^{Ar}$), 145.6 (C, N—C$^{Ar}$), 135.3 (C, C$^{Ar}$), 131.5 (C, C$^{Ar}$), 129.1 (CH, C$^{Ar}$), 128.6 (CH, C$^{Ar}$), 126.8 (CH, C$^{Ar}$), 126.6 (CH, C$^{Ar}$), 126.5 (CH, C$^{Ar}$), 126.4 (CH, C$^{Ar}$), 125.3 (CH, C$^{Ar}$), 124.0 (CH, C$^{Ar}$), 117.4 (CH, C$^{Ar}$), 113.8 (CH, C$^{Ar}$), 40.3 (CH$_3$, Me).

Examples 29-35

Table 4

Example 29

N-(2-Pyridyl)morpholine (Table 4, Entry 1)

The above general procedure yielded, after flash chromatography on silica gel (pentane/MTBE, 85/15), 141 mg (86%) of the title compound.

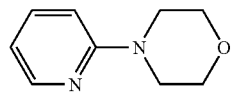

H NMR (300 MHz, CDCl$_3$): δ 8.20-8.18 (m, 1H, H$^{Ar}$), 7.51-7.45 (m, 1H, H$^{Ar}$), 6.66-6.60 (m, 2H, H$^{Ar}$), 3.80 (t, J=4.8 Hz, 4H, O—CH$_2$), 3.48 (t, J=4.8 Hz, 4H, N—CH$_2$).

$^{13}$C NMR (75 MHz, CDCl$_3$): δ 159.5 (C, C$^{Ar}$—N), 147.5 (CH, C$^{Ar}$), 137.3 (C, C$^{Ar}$), 113.6 (CH, C$^{Ar}$), 106.8 (CH, C$^{Ar}$), 66.6 (CH$_2$, O—CH$_2$), 45.5 (CH$_2$, N—CH$_2$).

Example 30

N-(2-Pyridyl)piperidine (Table 4, Entry 2)

The above general procedure yielded, after flash chromatography on silica gel (pentane/MTBE, 90/10), 154 mg (95%) of the title compound.

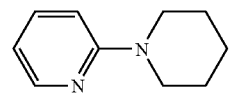

$^1$H NMR (300 MHz, CDCl$_3$): δ 8.16 (d, J=1.4 Hz, 1H, =CH—N), 7.38 (t, J=8.7 Hz, 1H, H$^{Ar}$), 6.59 (d, J=8.7 Hz, 1H, H$^{Ar}$), 6.50 (t, J=1.4 Hz, 1H, H$^{Ar}$), 3.49 (s broad, 4H, CH$_2$—N), 1.60 (s broad, 6H, CH$_2$).

$^{13}$C NMR (75 MHz, CDCl$_3$): δ 159.6 (C, C$^{Ar}$—N), 147.8 (CH, C$^{Ar}$—N), 137.1 (CH, C$^{Ar}$), 112.2 (CH, C$^{Ar}$), 106.9 (C, C$^{Ar}$), 46.2 (CH$_2$, CH$_2$—N), 25.4 (CH$_2$, CH$_2$), 25.7 (CH$_2$, CH$_2$).

Example 31

N-(3-Pyridyl)piperidine (Table 4, Entries 3 and 4)

A) The above general procedure with the aryl chloride yielded, after flash chromatography on silica gel (pentane/MTBE, 80/20), 128 mg (79%) of the title compound.

B) The above general procedure with the aryl bromide yielded, after flash chromatography on silica gel (pentane/MTBE, 80/20), 141 mg (87%) of the title compound.

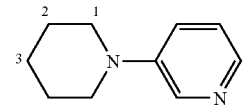

$^1$H NMR (300 MHz, CDCl$_3$): δ 8.30 (s, 1H, =CH—N), 8.05 (d, J=4.5 Hz, 1H, =CH—N), 7.19-7.10 (m, 2H, H$^{Ar}$), 3.18 (t, J=5.1 Hz, 4H, H$^1$), 1.75-1.67 (m, 4H, H$^2$), 1.63-1.57 (m, 2H, H$^3$).

$^{13}$C NMR (75 MHz, CDCl$_3$): δ 147.9 (C, N—C$^{Ar}$), 140.2 (CH, C$^{Ar}$), 139.1 (CH, C$^{Ar}$), 123.5 (CH, C$^{Ar}$), 122.7 (CH, C$^{Ar}$), 50.0 (CH$_2$, C$^1$), 25.7 (CH$_2$, C$^2$), 24.2 (CH$_2$, C$^3$).

Example 32

N-(3-Pyridyl)morpholine (Table 4, Entry 5)

The above general procedure yielded, after flash chromatography on silica gel (pentane/MTBE, 80/20), 144 mg (88%) of the title compound.

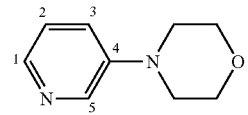

$^1$H NMR (400 MHz, CDCl$_3$): δ 8.31 (s, 1H, H$^5$), 8.14-8.12 (m, 1H, H$^1$), 7.19-7.10 (m, 2H, H$^2$+H$^3$), 3.88 (t, J=4.4 Hz, 4H, O—CH$_2$), 3.19 (t, J=4.4 Hz, 4H, N—CH$_2$).

$^{13}$C NMR (100 MHz, CDCl$_3$): δ 146.9 (C, C$^4$), 141.0 (CH, C$^{Ar}$), 138.3 (CH, C$^{Ar}$), 123.5 (CH, C$^{Ar}$), 122.0 (CH, C$^{Ar}$), 66.6 (CH$_2$, O—CH$_2$), 48.6 (CH$_2$, N—CH$_2$).

Example 33

N,N-Dibutyl-N-(2-pyridyl)amine (Table 4, Entry 6)

The above general procedure yielded, after flash chromatography on silica gel (pentane/DCM, 90/10), 178 mg (86%) of the title compound.

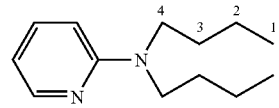

$^1$H NMR (300 MHz, CDCl$_3$): δ 8.03 (d, J=3.3 Hz, 1H, =CH—N), 7.27-7.23 (m, 1H, H$^{Ar}$), 6.35-6.30 (m, 2H, H$^{Ar}$), 3.32 (t, J=5.7 Hz, 4H, H$^4$), 1.51-1.43 (m, 4H, H$^3$), 1.33-1.20 (m, 4H, H$^2$), 0.85 (t, J 5.1 Hz, 6H, H$^1$).

$^{13}$C NMR (75 MHz, CDCl$_3$): δ 158.0 (C, C$^{Ar}$—N), 148.1 (CH, C$^{Ar}$—N), 136.8 (CH, C$^{Ar}$), 110.7 (CH, C$^{Ar}$), 105.5 (CH, C$^{Ar}$), 48.5 (CH$_2$, C$^4$), 29.9 (CH$_2$, C$^3$), 20.4 (CH$_2$, C$^2$), 14.1 (CH$_3$, C$^1$).

Example 34

N-Methyl-N-phenyl-N-(2-pyridyl)amine (Table 4, Entry 7)

The above general procedure yielded, after flash chromatography on silica gel (pentane, DCM, 90/10), 168 mg (91%) of the title compound.

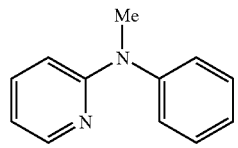

$^1$H NMR (300 MHz, CDCl$_3$): δ 8.22 (d, J=2.7 Hz, 1H, =CH—N), 7.34 (t, J=6.0 Hz, 1H, H$^{Ar}$), 7.23-7.14 (m, 2H, H$^{Ar}$), 6.55 (t, J=3.9 Hz, 1H, H$^{Ar}$), 6.50 (d, J=6.6 Hz, 4H, H$^{Ar}$), 3.45 (s, 3H, Me).

$^{13}$C NMR (75 MHz, CDCl$_3$): δ 158.6 (C, N—C$^{Ar}$—N), 147.6 (CH, C$^{Ar}$—N), 146.7 (C, C$^{Ar}$—N), 136.3 (CH, C$^{Ar}$), 129.5 (CH, C$^{Ar}$), 126.1 (CH, C$^{Ar}$), 125.2 (CH, C$^{Ar}$), 112.9 (CH, C$^{Ar}$), 108.9 (CH, C$^{Ar}$), 38.2 (CH$_3$, Me).

Example 35

N-Methyl-N-phenyl-N-(3-quinolyl)amine (Table 4, Entry 8)

The above general procedure yielded, after flash chromatography on silica gel (pentane/DCM, 95/5), 225 mg (96%) of the title compound.

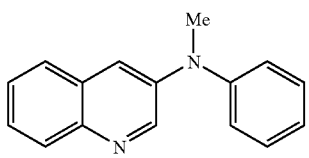

$^1$H NMR (400 MHz, CDCl$_3$): δ 8.68 (d, J=3.2 Hz, 1H, H$^{Ar}$), 8.00 (d, J=8.4 Hz, 1H, H$^{Ar}$), 7.59 (d, J=7.6 Hz, 1H, H$^{Ar}$), 7.48-7.38 (m, 3H, H$^{Ar}$), 7.28 (t, J=8.0 Hz, 2H, H$^{Ar}$), 6.58 (d, J=7.8 Hz, 2H, H$^{Ar}$), 7.09-7.02 (m, 3H, H$^{Ar}$), 3.32 (s, 3H, Me).

$^{13}$C NMR (100 MHz, CDCl$_3$): δ 148.0 (C, C$^{Ar}$), 146.1 (CH, C$^{Ar}$), 143.1 (C, C$^{Ar}$), 142.3 (C, C$^{Ar}$), 129.6 (CH, C$^{Ar}$), 129.0 (CH, C$^{Ar}$), 126.9 (CH, C$^{Ar}$), 126.51 (CH, C$^{Ar}$), 126.45 (CH, C$^{Ar}$), 123.3 (CH, C$^{Ar}$), 122.2 (CH, C$^{Ar}$), 119.2 (CH, C$^{Ar}$), 40.4 (CH$_3$, Me).

Examples 36-46

Table 5

α-Ketone Arylation of Aryl Halides.

General procedure: In a glove box, (IPr)Pd(acac)Cl (0.01 mmol, 6.3 mg), sodium tert-butoxide (1.5 mmol, 144 mg) and anhydrous toluene (1 mL) were added in turn to a vial equipped with a magnetic bar, and sealed with a screw cap fitted with a septum. Outside the glove box, the ketone (1.1 mmol) and the aryl halide (1 mmol) were injected in turn through the septum. If one of the two starting materials was a solid, it was added to the vial inside the glove box and toluene and the second starting material were added outside the glove box under argon. The reaction mixture was then stirred at 60° C. When the reaction reached completion, or no further conversion could be observed by Gas Chromatography (GC), water was added to the reaction mixture, the organic layer was extracted with tert-butylmethyl ether (MTBE), dried over magnesium sulfate and the solvent was evaporated in vacuo. When necessary the product was purified by flash chromatography on silica gel. The reported yields are the average of at least two runs.

Example 36

1-Phenyl-2-o-tolylethanone (Table 5, Entries 1 and 2)

A) The above general procedure with the aryl chloride yielded, after flash chromatography on silica gel (pentane/MTBE, 90/10), 187 mg (89%) of the title compound.

B) The above general procedure with the aryl bromide yielded, after flash chromatography on silica gel (pentane/MTBE, 90/10), 189 mg (90%) of the title compound.

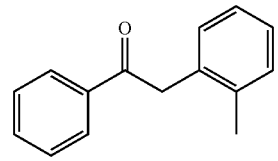

$^1$H NMR (300 MHz, CDCl$_3$): δ 7.98 (d, J=7.2 Hz, 2H, H$^{Ar}$), 7.52-7.42 (m, 1H, H$^{Ar}$), 7.40-7.37 (m, 2H, H$^{Ar}$), 7.16-7.07 (m, 4H, H$^{Ar}$), 4.23 (s, 2H, CH$_2$), 2.21 (s, 3H, CH$_3$).

$^{13}$C NMR (75 MHz, CDCl$_3$): δ 197.4 (C, C=O), 136.9 (C, C$^{Ar}$), 133.5 (C, C$^{Ar}$), 133.1 (CH, C$^{Ar}$), 130.3 (CH, C$^{Ar}$), 128.7 (CH, C$^{Ar}$), 128.5 (CH, C$^{Ar}$), 128.3 (CH, C$^{Ar}$), 128.1 (C, C$^{Ar}$), 127.2 (CH, C$^{Ar}$), 126.1 (CH, C$^{Ar}$), 43.4 (CH$_2$, CH$_2$), 19.8 (CH$_3$, CH$_3$).

Example 37

1,2-Diphenylpropan-1-one (Table 5, Entry 3)

The above general procedure yielded, after flash chromatography on silica gel (pentane/MTBE, 80/20), 206 mg (98%) of the title compound.

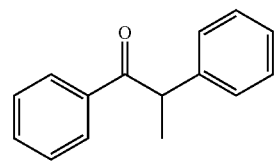

$^1$H NMR (300 MHz, CDCl$_3$): δ 7.93 (d, J=7.2 Hz, 2H, H$^{Ar}$), 7.43 (t, J=7.2 Hz, 1H, H$^{Ar}$), 7.34 (t, J=7.5 Hz, 2H, H$^{Ar}$), 7.26 (d, J=3.6 Hz, 2H, H$^{Ar}$), 7.21-7.16 (m, 1H, H$^{Ar}$), 4.66 (q, J=6.9 Hz, 1H, CH—CH$_3$), 1.52 (d, J=6.9 Hz, 3H, CH—CH$_3$).

$^{13}$C NMR (75 MHz, CDCl$_3$): δ 200.5 (C, C=O), 141.8 (C, C$^{Ar}$), 132.9 (C, C$^{Ar}$) 129.2 (CH, C$^{Ar}$), 129.0 (CH, C$^{Ar}$), 128.7 (CH, C$^{Ar}$), 128.0 (CH, C$^{Ar}$), 127.1 (CH, C$^{Ar}$), 48.2 (CH, CH), 19.7 (CH$_3$, CH$_3$).

Example 38

1-Phenyl-2-[4-(trifluoromethyl)phenyl]propan-1-one (Table 5, Entry 4)

The above general procedure yielded, after flash chromatography on silica gel (pentane/EtOAc, 90/10), 259 mg (93%) of the title compound.

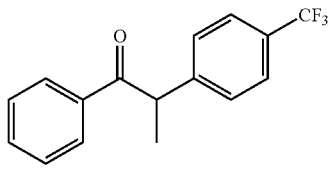

$^1$H NMR (300 MHz, CDCl$_3$): δ 7.93 (d, J=7.2 Hz, 2H, H$^{Ar}$), 7.55 (d, J=8.4 Hz, 2H, H$^{Ar}$), 7.51-7.48 (m, 1H, H$^{Ar}$), 7.43-7.38 (m, 4H, H$^{Ar}$), 4.77 (q, J=6.9 Hz, 1H, CH—CH$_3$), 1.55 (d, J=6.9 Hz, 3H, CH—CH$_3$).
$^{13}$C NMR (75 MHz, CDCl$_3$): δ 199.9 (C, C=O), 145.6 (C, CF$_3$), 136.4 (C, C$^{Ar}$—CF$_3$), 133.9 (C, C$^{Ar}$), 133.4 (CH, C$^{Ar}$), 130.4 (C, C$^{Ar}$), 128.92 (CH, C$^{Ar}$), 128.88 (CH, C$^{Ar}$), 128.4 (CH, C$^{Ar}$), 128.4 (CH, C$^{Ar}$), 47.8 (CH, CH—CH$_3$), 19.6 (CH$_3$, CH—CH$_3$).

Example 39

2-Phenyl-α-tetralone (Table 5, Entries 5 and 6)

A) The above general procedure with the aryl chloride yielded, after flash chromatography on silica gel (pentane/MTBE, 90/10), 138 mg (62%) of the title compound.
B) The above general procedure with the aryl bromide yielded, after flash chromatography on silica gel (pentane/MTBE, 90/10), 160 mg (72%) of the title compound.

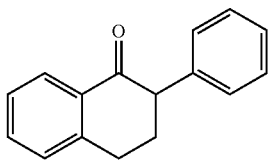

$^1$H NMR (300 MHz, CDCl$_3$): δ 7.09 (d, J=7.8 Hz, 1H, H$^{Ar}$), 7.49 (t, J=7.2 Hz, 1H, H$^{Ar}$), 7.35-7.23 (m, 4H, H$^{Ar}$), 7.18 (d, J=7.2 Hz, 3H, H$^{Ar}$), 3.79 (t, J=7.8 Hz, 1H, C(O)—CH), 3.14-2.99 (m, 2H, C$^{Ar}$—CH$_2$), 2.46-2.39 (m, 2H, CH—CH$_2$).
$^{13}$C NMR (75 MHz, CDCl$_3$): δ 198.2 (C, C=O), 144.2 (C, C$^{Ar}$), 139.9 (C, C$^{Ar}$), 133.5 (CH, C$^{Ar}$), 128.9 (CH, C$^{Ar}$), 128.6 (CH, C$^{Ar}$), 128.5 (CH, C$^{Ar}$), 127.9 (CH, C$^{Ar}$), 127.0 (CH, C$^{Ar}$), 126.9 (CH, C$^{Ar}$), 54.5 (CH, C(O)—CH), 31.3 (CH$_2$), 28.9 (CH$_2$).

Example 40

2-(2-Methoxyphenyl)-1-phenylpropan-1-one (Table 5, Entries 7 and 8)

A) The above general procedure with the aryl chloride yielded, after flash chromatography on silica gel (pentane/MTBE, 85/15), 219 mg (91%) of the title compound.
B) The above general procedure with the aryl chloride yielded, after flash chromatography on silica gel (pentane/MTBE, 85/15), 199 mg (83%) of the title compound.

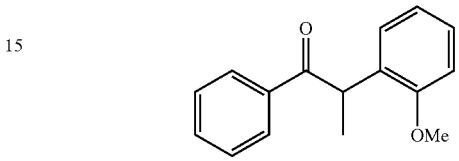

$^1$H NMR (300 MHz, CDCl$_3$): δ 7.94 (d, J=7.8 Hz, 2H, H$^{Ar}$), 7.38 (t, J=6.9 Hz, 1H, H$^{Ar}$), 7.31 (t, J=6.6 Hz, 2H, H$^{Ar}$), 7.17-7.09 (m, 2H, H$^{Ar}$), 6.86-6.81 (m, 2H, H$^{Ar}$), 5.07 (q, J=6.8 Hz, 1H, CH—CH$_3$), 3.83 (s, 3H, OCH$_3$), 1.46 (d, J=6.8 Hz, 3H, CH—CH$_3$).
$^{13}$C NMR (75 MHz, CDCl$_3$): δ 201.5 (C, C=O), 155.9 (C, C$^{Ar}$—O), 136.7 (C, C$^{Ar}$), 132.6 (C, C$^{Ar}$), 128.6 (CH, C$^{Ar}$), 128.4 (CH, C$^{Ar}$), 128.2 (CH, C$^{Ar}$), 128.1 (CH, C$^{Ar}$), 128.0 (CH, C$^{Ar}$), 121.2 (CH, C$^{Ar}$), 110.9 (CH, C$^{Ar}$), 55.6 (CH, CH—CH$_3$), 40.5 (CH$_3$, OCH$_3$), 17.7 (CH$_3$, CH—CH$_3$).

Example 41

1-Phenyl-2-(2,4,6-trimethylphenyl)propan-1-one (Table 5, Entry 9)

The above general procedure yielded, after flash chromatography on silica gel (pentane/MTBE, 90/10), 212 mg (84%) of the title compound.

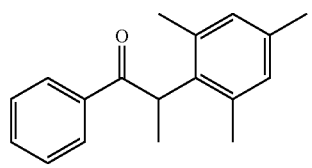

$^1$H NMR (300 MHz, CDCl$_3$): δ 7.70 (d, J=8.4 Hz, 2H, H$^{Ar}$), 7.37 (t, J=7.2 Hz, 1H, H$^{Ar}$), 7.25 (t, J=7.5 Hz, 2H, H$^{Ar}$), 6.77 (s, 2H, H$^{Ar}$), 4.47 (q, J=6.6 Hz, 1H, CH—CH$_3$), 2.24 (s, 6H, C$^{Ar}$—CH$_3$), 2.19 (s, 3H, C$^{Ar}$—CH$_3$), 1.48 (d, J=6.6 Hz, 3H, CH—CH$_3$).
$^{13}$C NMR (75 MHz, CDCl$_3$): δ 202.4 (C, C=O), 137.0 (C, C$^{Ar}$), 136.2 (C, C$^{Ar}$), 135.6 (C, C$^{Ar}$), 132.5 (CH, C$^{Ar}$), 130.5 (CH, C$^{Ar}$), 128.4 (CH, C$^{Ar}$), 46.0 (CH, CH—CH$_3$), 29.8 (CH$_3$, CA$^{Ar}$—CH$_3$), 20.8 (CH$_3$, C$^{Ar}$—CH$_3$), 20.6 (CH$_3$, C$^{Ar}$—CH$_3$), 15.2 (CH$_3$, CH—CH$_3$)

Example 42

2-(o-Tolyl)-α-tetralone (Table 5, Entry 10)

The above general procedure yielded, after flash chromatography on silica gel (pentane/MTBE, 90/10), 206 mg (87%) of the title compound.

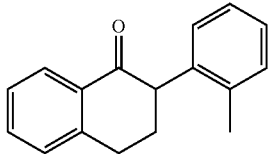

$^1$H NMR (300 MHz, CDCl$_3$): δ 8.10 (d, J=7.8 Hz, 1H, H$^{Ar}$), 7.51 (t, J=7.1 Hz, 1H, H$^{Ar}$), 7.37-7.29 (m, 2H, H$^{Ar}$), 7.25-7.15 (m, 3H, H$^{Ar}$), 7.07-7.04 (m, 1H, H$^{Ar}$), 3.98 (dd, J=11.4, 4.8 Hz, 1H, C(O)—CH), 3.16-3.04 (m, 2H, C$^{Ar}$—CH$_2$), 2.53-2.27 (m, 2H, CH—CH$_2$), 2.32 (s, 3H, CH$_3$).

$^{13}$C NMR (75 MHz, CDCl$_3$): δ 198.2 (C, C=O), 164.3 (C, C$^{Ar}$), 144.3 (C, C$^{Ar}$), 138.9 (C, C$^{Ar}$), 136.7 (C, C$^{Ar}$), 133.6 (CH, C$^{Ar}$), 130.8 (CH, C$^{Ar}$), 129.0 (CH, C$^{Ar}$), 128.0 (CH, C$^{Ar}$), 127.8 (CH, C$^{Ar}$), 127.1 (CH, C$^{Ar}$), 127.0 (CH, C$^{Ar}$), 126.4 (CH, C$^{Ar}$), 51.7 (CH, C(O)—CH), 30.6 (CH$_2$, CH$_2$), 29.7 (CH$_2$, CH$_2$), 20.1 (CH$_3$, CH$_3$).

Example 43

2-(2,6-Dimethyl-phenyl)-1-(1-methyl-1H-pyrrol-2-yl)-ethanone (Table 5, Entry 11)

The above general procedure yielded, after a pentane wash, 218 mg (96%) of the title compound.

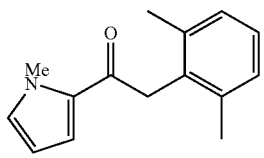

$^1$H NMR (300 MHz, CDCl$_3$): δ 7.12-7.10 (m, 1H, H$^{Ar}$), 7.04-7.02 (m, 3H, H$^{Ar}$), 6.75 (s, 1H, H$^{Ar}$), 6.14-6.12 (m, 1H, H$^{Ar}$), 4.28 (s, 2H, C(O)—CH$_2$), 3.96 (s, 3H, N—CH$_3$) 2.32 (s, 6H, C$^{Ar}$—CH$_3$).

$^{13}$C NMR (75 MHz, CDCl$_3$): δ 188.0 (C, C=O), 137.3 (C, C$^{Ar}$), 132.9 (C, C$^{Ar}$), 131.0 (CH, C$^{Ar}$), 130.7 (C, C$^{Ar}$), 128.0 (CH, C$^{Ar}$), 126.8 (CH, C$^{Ar}$), 118.8 (CH, C$^{Ar}$), 108.0 (CH, C$^{Ar}$), 39.7 (CH$_2$, C(O)—CH$_2$), 37.8 (CH$_3$, N—CH$_3$), 20.6 (CH$_3$, C$^{Ar}$—CH$_3$).

Anal. Calcd. for C$_{15}$H$_{17}$NO (MW 227.30): C, 79.26; H, 7.54; N, 6.16. Found: C, 79.39; H, 7.24; N, 5.74.

Example 44

2-(Naphthalen-1-yl)-1-phenyl-propan-1-one (Table 5, Entry 12)

The above general procedure yielded, after a pentane wash, 250 mg (96%) of the title compound.

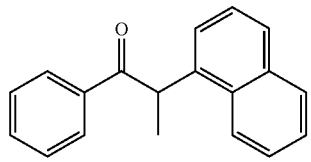

$^1$H NMR (300 MHz, CDCl$_3$): δ 8.21 (d, J=8.1 Hz, 1H, H$^{Ar}$), 7.84 (d, J=7.5 Hz, 2H, H$^{Ar}$), 7.65 (d, J=8.1 Hz, 1H, H$^{Ar}$), 7.57 (t, J=7.8 Hz, 1H, H$^{Ar}$), 7.48 (t, J=7.2 Hz, 1H, H$^{Ar}$), 7.34-7.21 (m, 2H, H$^{Ar}$), 7.20-7.17 (m, 2H, H$^{Ar}$), 5.34 (q, J=6.7 Hz, 1H, CH—CH$_3$), 1.61 (d, J=6.7 Hz, 3H, CH—CH$_3$).

$^{13}$C NMR (75 MHz, CDCl$_3$): δ 200.7 (C, C=O), 138.1 (C, C$^{Ar}$), 136.5 (C, C$^{Ar}$), 134.5 (C, C$^{Ar}$), 132.7 (CH, C$^{Ar}$), 130.7 (C, C$^{Ar}$), 129.4 (CH, C$^{Ar}$), 128.7 (CH, C$^{Ar}$), 128.5 (CH, C$^{Ar}$), 127.7 (CH, C$^{Ar}$), 126.8 (CH, C$^{Ar}$), 125.9 (CH, C$^{Ar}$), 125.1 (CH, C$^{Ar}$), 122.6 (CH, C$^{Ar}$), 43.8 (CH, CH—CH$_3$), 18.6 (CH$_3$, CH—CH$_3$).

Example 45

2-(Naphthalen-2-yl)-1-phenylpropan-1-one (Table 5, Entry 13)

The above general procedure yielded, after a pentane wash, 253 mg (97%) of the title compound.

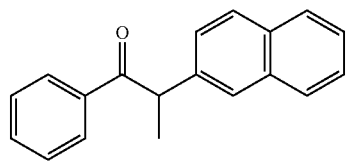

$^1$H NMR (300 MHz, CDCl$_3$): δ 7.96 (d, J=5.7 Hz, 2H, H$^{Ar}$), 7.73-7.69 (m, 4H, H$^{Ar}$), 7.39-7.31 (m, 4H, H$^{Ar}$), 7.26 (t, J=5.7 Hz, 2H, H$^{Ar}$), 4.77 (q, J=5.1 Hz, 1H, CH—CH$_3$), 1.58 (d, J=5.1 Hz, 3H, CH—CH$_3$).

$^{13}$C NMR (75 MHz, CDCl$_3$): δ 200.3 (C, C=O), 139.1 (C, C$^{Ar}$), 136.5 (C, C$^{Ar}$), 133.7 (C, C$^{Ar}$), 132.9 (CH, C$^{Ar}$), 132.4 (C, C$^{Ar}$), 128.9 (CH, C$^{Ar}$), 128.8 (CH, C$^{Ar}$), 128.5 (CH, C$^{Ar}$), 127.8 (CH, C$^{Ar}$), 127.7 (CH, C$^{Ar}$), 126.5 (CH, C$^{Ar}$), 125.2 (CH, C$^{Ar}$), 126.0 (CH, C$^{Ar}$), 125.8 (CH, C$^{Ar}$), 48.0 (CH, CH—CH$_3$), 19.6 (CH$_3$, CH—CH$_3$).

Anal. Calcd. for C$_{19}$H$_{16}$O (MW 260.33): C, 87.66; H, 6.19. Found: C, 87.90; H, 6.35.

Example 46

2-(Biphenyl-4-yl)-1-phenylpropan-1-one (Table 5, Entry 14)

The above general procedure yielded, after a pentane wash, 272 mg (95%) of the title compound.

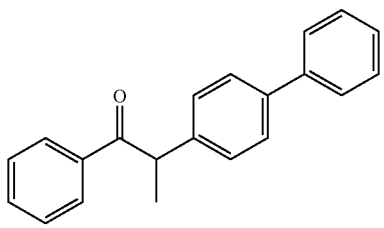

$^1$H NMR (300 MHz, CDCl$_3$): δ 7.97 (d, J=5.4 Hz, 2H, H$^{Ar}$), 7.52-7.47 (m, 4H, H$^{Ar}$), 7.43 (d, J=5.4 Hz, 2H, H$^{Ar}$), 7.39-7.33 (m, 5H, H$^{Ar}$), 7.29 (d, J=5.7 Hz, 1H, H$^{Ar}$), 4.72 (q, J=5.1 Hz, 1H, CH—CH$_3$), 1.55 (d, J=5.1 Hz, 3H, CH—CH$_3$).

$^{13}$C NMR (75 MHz, CDCl$_3$): δ 200.5 (C, C=O), 140.8 (C, C$^{Ar}$), 140.6 (C, C$^{Ar}$), 139.9 (C, C$^{Ar}$), 136.6 (C, C$^{Ar}$), 133.0 (C, C$^{Ar}$), 128.9 (CH, C$^{Ar}$), 128.8 (CH, C$^{Ar}$), 128.7 (CH, C$^{Ar}$), 128.3 (CH, $C^{Ar}$), 127.8 (CH, $C^{Ar}$), 127.4 (CH, $C^{Ar}$), 127.1 (CH, $C^{Ar}$), 47.6 (CH, CH—$CH_3$), 19.6 ($CH_3$, CH—$CH_3$).

Example 47

The following general procedure was followed to evaluate the conversion percentage using the catalysts discussed below.

General procedure: In a glove box, one of the catalysts (IPr)Pd(acac)Cl, (IPr)Pd(acacdiPh)Cl, (IPr)Pd(acactBu)Cl, (IPr)Pd(acacMePh)Cl, and (IPr)Pd(acacF)Cl (0.01 mmol), was combined with potassium tert-butoxide (1.1 mmol, 124 mg) and anhydrous dimethoxyethane (DME) (1 mL) were added in turn to a vial equipped with a magnetic bar, and sealed with a screw cap fitted with a septum. Outside the glovebox, dibutylamine (185 µL, 1.1 mmol) and 4-chlorotoluene (118 µL, 1 mmol) were injected in turn through the septum. The reaction mixture was then stirred at 50° C. The reaction was monitored by gas chromatograph. The percent conversions shown in FIG. 1 represent the average of three runs.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims. It will also be realized that while the present invention has been described with reference to specific details of particular embodiments thereof; it is not intended that such details be regarded as limitations upon the scope of the invention except, as stated above, insofar as and to the extent that they are included in the accompanying claims.

What is claimed is:

1. A palladium complex characterized by the general formula:

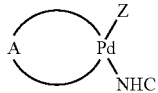

where A is a bidentate monoanionic ligand, NHC is a nucleophilic heterocyclic carbene, and Z is an anionic ligand.

2. The palladium complex of claim 1, where Z is selected from Cl, Br, I, OAc, OMs, OTf, OTs, $O_2CCF_3$, acetylacetonate (acac), trifluoroacetylacetonate, hexafluoroacetylacetonate (hfacac); dibenzoylmethanate (dbm), benzoylacetonate (bac), or tetramethylheptanedionate (trmhd).

3. The palladium complex of claim 1, where A is represented by:

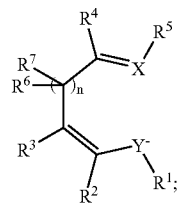

each of X and Y are independently selected from O, N, or S and where $R^1$, $R^2$, $R^3$, $R^4$, $R^5$, $R^6$ and $R^7$ independently represent hydrogen, methyl, linear or branched $C_2$-$C_{10}$ alkyl, $C_3$-$C_{10}$ cycloalkyl, $C_7$-$C_{20}$ aralkyl, or $C_6$-$C_{24}$ aryl or substituted aryl, subject to the proviso that $R^1$ and $R^5$ are only present when X and/or Y is N; n represents an integer of 0, 1, or 2; and Z is selected from Cl, Br, I, OAc, OMs, OTf, OTs, $O_2CCF_3$, acetylacetonate (acac), trifluoroacetylacetonate, hexafluoroacetylacetonate (hfacac); dibenzoylmethanate (dbm), benzoylacetonate (bac), or tetramethylheptanedionate (tmhd).

4. The palladium complex of claim 3, where X—Y is a hemilabile group.

5. The palladium complex of claim 3 where X—Y is selected from β-diketonato (O—O), β-diketimiato (N—N), β-ketininato (N—O) or Schiff base (N—O) ligands.

6. The palladium complex of claim 3, wherein X—Y is the X—Y(a) and X—Y(b) tautomers shown below:

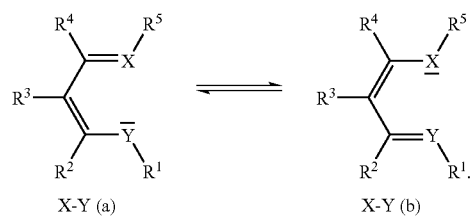

7. The palladium complex of claim 1, where A is one of the structures shown below:

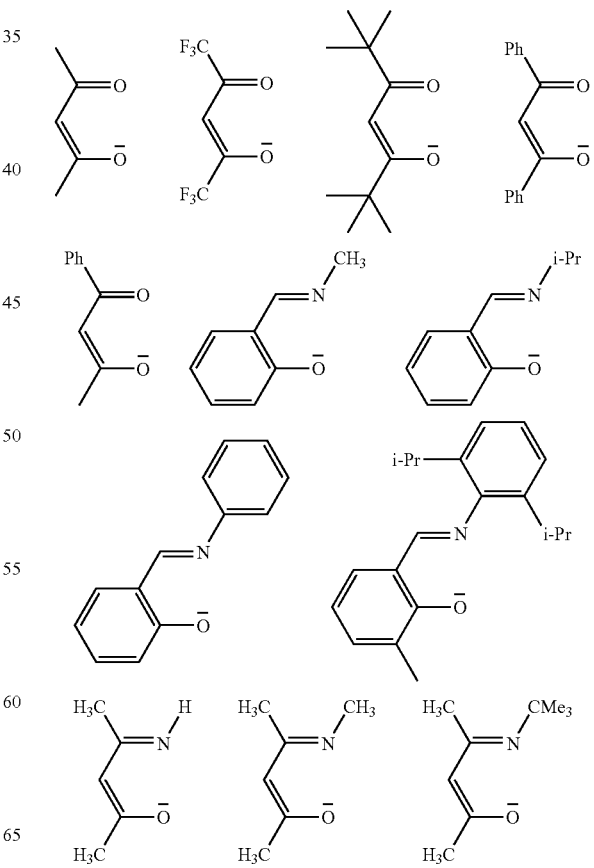

-continued

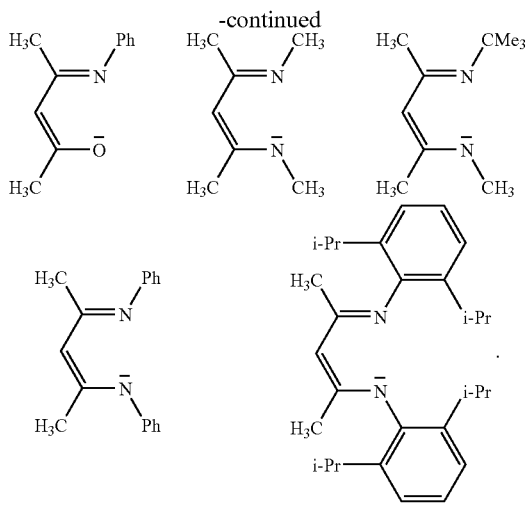

8. The palladium complex of claim 7, where NHC is one of A, B or C,

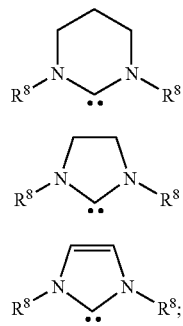

each R⁸ is independently one of of hydrogen, methyl, linear or branched $C_2$-$C_{10}$ alkyl, $C_3$-$C_{10}$ cycloalkyl, $C_7$-$C_{20}$ aralkyl, or $C_6$-$C_{24}$ aryl or substituted aryl.

9. The palladium complex of claim 7, where NHC is

each R⁸ is one of methyl, ethyl, isopropyl, isobutyl, tert-butyl, cyclohexyl, norbornyl, adamantyl, 2,6-dimethylphenyl, 2,4,6-trimethylphenyl, 2,6-diisopropylphenyl or 2-methylphenyl.

10. The palladium complex of claim 1, where such complex is one of
(NHC)Pd(acac)₂, (NHC)Pd(acac)Cl, (NHC)Pd(hfacac)₂ (NHC)Pd (hfacac)Cl,
(NHC)Pd(dbm)₂, NHC)Pd(dbm)Cl, (NHC)Pd(tmhd)₂, (NHC)Pd(tmhd)Cl,
(NHC)Pd(bac)₂ or NHC)Pd(bac)Cl, where NHC is one of
IMes (N,N'-bis(2,4,6-trimethylphenyl)imidazol)-2-ylidene),
IMes (N,N'-bis(2,4,6-trimethylphenyl)-4,5-dihydroimidazol)-2-ylidene),
IPr (N,N'-bis(2,6-diisopropylphenyl)idazol)-2-ylidene),
sIPr (N,N'-bis(2,6-diisopropylphenyl)-4,5-dihydroimidazol)-2-ylidene),
IAd (N,N'-bis(adamantyl)imidazol-2-ylidene),
ICy (N,N'-bis(cyclohexyl)imidazol-2-ylidene), or
ItBu (N,N'-bis(tert-butyl)imidazol-2-ylidene).

11. The palladium complex of claim 1, where such complex is (IPr)Pd(acac)Cl, represented as:

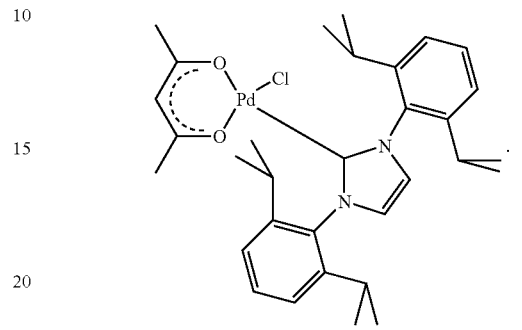

12. A process for the preparation of the palladium complex of claim 1 comprising:
reacting a group VIII metal source with an NHC in an organic solvent at an appropriate temperature for an appropriate period of time, where such reacting forms the palladium complex.

13. The process of claim 12 further comprising isolating the palladium complex.

14. The process of claim 12, wherein the Group VIII metal sources is Pd(acac)₂, the organic solvent is diethyl ether, and the reaction temperature is ambient.

15. The process of claim 12, where the NHC is one of A, B or C

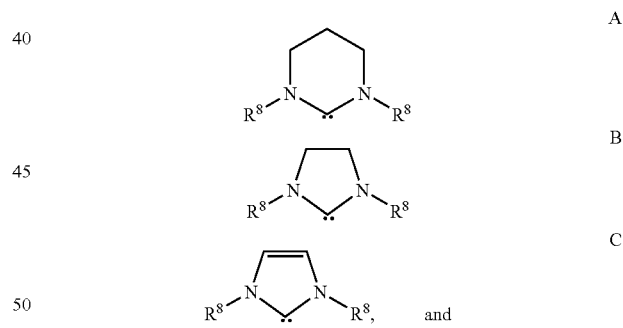

each R⁸ is independently one of hydrogen, methyl, linear or branched $C_2$-$C_{10}$ alkyl, $C_3$-$C_{10}$ cycloalkyl, $C_7$-$C_{20}$ aralkyl, or $C_6$-$C_{24}$ aryl or substituted aryl.

16. The process of claim 12, where NHC is:

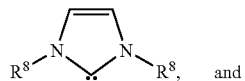

each R⁸ is one of methyl, ethyl, isopropyl, isobutyl, tert-butyl, cyclohexyl, norbornyl, adamantyl, 2,6-dimethylphenyl, 2,4,6-trimethylphenyl, 2,6-diisopropylphenyl or 2-methylphenyl.

17. A process for the preparation of a palladium complex of claim 1 comprising:
providing a solution of a palladium metal source and an imidazolium salt in an organic solvent;
heating the solution to an appropriate temperature for an appropriate period of time; and
isolating the complex.

18. The process of claim 17, where the palladium metal source is Pd(acac)₂, the imidazolium salt is I-PrHCl, the organic solvent is dioxane, the reaction temperature is 100° C., the appropriate period of time is 6 hours and where the complex isolated is (I-Pr)Pd(acac)Cl.

19. The process of claim 17, where the palladium metal source is one of Pd(acac)₂, bis(trifluoroacetylacetonate)Pd, bis(hexafluoroacetylacetonate)Pd; bis(dibenzoylmethanate)Pd, bis(benzoylacetonate)Pd, bis(tetramethylheptanedionate)Pd or bis(tropolonato)palladium(II).

20. A process of forming a carbon-carbon or a carbon-heteroatom bond comprising:
providing a palladium complex represented by Formula I:

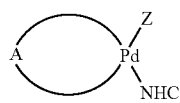

where NHC is a nucleophilic heterocyclic carbene; Z is an anionic ligand; and A is a bidentate monoanionic ligand represented by Formula II:

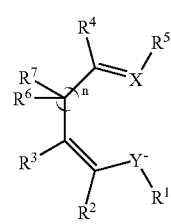

and further where each of X and Y is independently one of O, N, or S and where $R^1$, $R^2$, $R^3$, $R^4$, $R^5$, $R^6$ and $R^7$ each independently represent hydrogen, methyl, linear or branched $C_2$-$C_{10}$ alkyl, $C_3$-$C_{10}$ cycloalkyl, $C_7$-$C_{20}$ aralkyl, or $C_6$-$C_{24}$ aryl or substituted aryl, subject to the proviso that $R^1$ and $R^5$ are only present when X and/or Y is N; n represents an integer of 0, 1, or 2; and Z is one of Cl, Br, I, OAc, OMs, OTf, OTs, O₂CCF₃, acetylacetonate (acac), trifluoroacetylacetonate, hexafluoroacetylacetonate (hfacac); dibenzoylmethanate (dbm), benzoylacetonate (bac), or tetramethylheptanedionate (tmhd); and
forming a carbon-carbon or carbon-heteroatom bond using one of the Suzuki, Suzuki-Miyaura, Murahashi, Kumada, Kumada-Corriu, Kumada-Tamao, Nozaki, Nozaki-Oshima, Negishi, Hiyama, Tamao-Kumada, Hiyama-Hatanaka, Stille, Migita-Kosugi, Buchwald-Hartwig, Murahashi, Cyanation, dehydrohalogenation, α-"Carbonyl" Arylation, Sonogashira , Cadiot-Chodkiewicz, Heck reactions, catalytic ether formation, catalytic α-arylations of ketones, dehalogenation, and catalytic thioether formation reactions, substrates and reactive partners thereof.

21. The process of claim 20, where the bonding forming reaction is either a Buchwald Hartwig aryl amination or an α-arylation of ketones.

22. The process of claim 20 in which the palladium complex employed is one of (NHC)Pd(acac)₂, (NHC)Pd(acac)Cl, (NHC)Pd(hfacac)₂ (NHC)Pd(ifacac)Cl,
(NHC)Pd(dbm)₂, (NHC)Pd(dbm)Cl, (NHC)Pd(tmhd)₂, (NHC)Pd(tmhd)Cl,
(NHC)Pd(bac), (NHC)Pd(bac)Cl, or (NHC)Pd(acac)X, where X is a halide or pseudohalide; and where NHC is one of
IMes (N,N'-bis(2,4,6-trimethylphenyl)imidazol)-2-ylidene),
sIMes (N,N'-bis(2,4,6-trethylphenyl)-4,5-dihydroimidazol)-2-ylidene),
IPr (N,N'-bis(2,6-diisopropylphenyl)imidazol)-2-ylidene),
sIPr (N,N'-bis(2,6-diisopropylphenyl)-4,5-dihydroimidazol)-2-ylidene),
IAd (N,N'-bis(adamantyl)imidazol-2-ylidene),
ICy (N,N'-bis(cyclohexyl)imidazol-2-ylidene), or
ItBu (N,N'-bis(tert-butyl)imidazol-2-ylidene).

23. The process of claim 22 in which the bond forming reaction is Buchwald Hartwig aryl amination, the palladium complex is (IPr)Pd(acac)Cl or (IPr)Pd(acac)Br and the aryl chloride or aryl bromide is one of 2-chloropyridine, 2,6-dimethylchlorobenzene, 4-chlorotoluene, 4-methoxychlorobenzene, 2-bromopyridine, 2,6-dimethylbromobenzene, or 6-methoxybromobenzene, and the amine is one- of aniline, dibutylamine, or morpholine.

24. The process of claim 22 in which the bond forming reaction is an α-ketone arylation, the palladium complex is (IPr)Pd(acac)Cl or (IPr)Pd(acac)Br and the aryl chloride or aryl bromide is one of chlorobenzene, 2,6-dimethylchlorobenzene, 4-4-chlorotoluene, 4-methoxychlorobenzene, 2-chloropyridine, 2-bromopyridine, 2,6-dimnethylbromobenzene, 6-methoxybromobenzene, respectively, and the ketone is one of cyclohexanone, methylphenyl ketone, ethylphenyl ketone, and methylnaphthyl ketone.

25. The process of claim 24 further comprising adding a base, where the base is selected from sodium tert-butoxide, potassium tert-butoxide, K₂CO₃, K₃PO₄, KF, and Cs₂CO₃.

26. The process of claim 20, wherein the substrate is selected from:
NBCH2Cl, NBCH2Br, NBCH2I, NBCH2QMs, NBCH2OTs, NBCH2OTf,
NBCH2Bpin, NBCH2Bcat, NBCH2-9-BBN, NBCH2Li, NBCH2MgBr,
NBCH2ZnBr, NBCH2SiF3, NBCH2BF3K, NBCH2B(OH)2, NBCH2CH2Cl,
NBCH2CH2Br, NBCH2CH2I, NBCH2CH2OMs, NBCH2CH2OTs,
NBCH2CH2OTf, NBCH2CH2Bpin, NBCH2CH2Bcat, NBCH2CH2-9-BBN,
NBCH2CH2Li, NBCH2CH2MgBr, NBCH2CH2ZnBr, NBCH2CH2SiF3,
NBCH2CH2BF3K, NBCH2CH2B(OH)2, NBC6H4B(OH)2, NBCH2C6H4B (OH)2,
NBCH2CH2C6H4B(OH)2, and NBC6H4BCH2(OH)2.

27. The process of claim 20, wherein the substrate is selected from any of the following monomers:

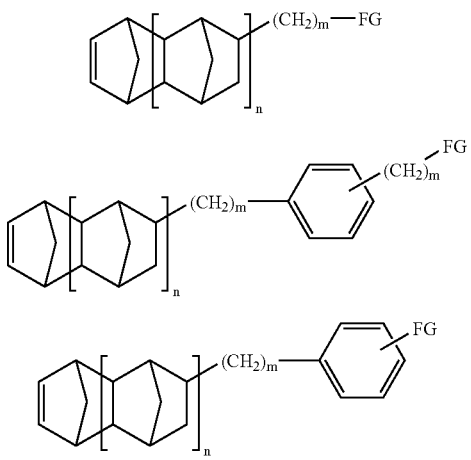

where n is selected from 0 or 1, m is selected from 0 to 5, and FG is selected from Cl, Br, I, OTf, OMs, OTs, ZnBr, MgBr, SiF$_3$, Si(OR)$_3$, B(OH)$_2$, Bcat, 9-BBN, Bpin, ketones, aldehydes, or amines.

28. A process for the preparation of a palladium complex of claim 1 comprising reacting a palladium metal source directly with an imidazolium salt to form the palladium complex.

29. The process of claim 28, including adding the palladium metal source and imidazolium salt to an organic solvent and refluxing the resultant mixture.

30. The process of claim 28, where the palladium metal source and the imidazolium salt are provided at a ratio of 1 equivalent palladium metal source: greater than 1 equivalent imidazolium salt.

31. The process of claim 28, where the reaction is carried out in an air atmosphere.

32. The process of claim 29, including heating the mixture to a temperature in the range of 50° C. to 150° C. and refluxing for a time in the range of 2 hours to 8 hours.

33. The process of claim 32, including heating the mixture to 100° C. and refluxing for 6 hours.

34. The process of claim 29, where the organic solvent is dioxane.

35. The process of claim 28, where the palladium metal source is selected from Pd(acac)$_2$, bis(trifluoroacetylacetonate)Pd, bis(hexafluoroacetylacetonate)Pd, or bis(tetramethylheptanedionate)Pd.

36. The process of claim 28, where the iruidazolium salt is selected from Ipr.HCl or Imes.HCl.

37. A palladium complex made by the process of claim 28.

38. The process of claim 23, wherein the product of the bond forming reaction is selected from N-4-(cyanophenyl) piperidine, N-(o-tolyl)morpholine, N-(2-methoxyphenyl) morpholine, N,N-dibutyl-N-(o-tolyl)amine, N-(2,6-diisopropylphenyl)-N-(o-tolyl)amine, N-(2,6-diisopropylphenyl)-N-(2,6-dimethylphenyl)amine, N-(2-naphthyl)piperidine, N-N-dibutyl-N-(4-methoxyphenyl)amine, N-(2,6-dimethylphenyl)-N-(o-tolyl)amine, N-(2,6-diisopropylphenyl)-N-(p-tolyl)amine, N-(2,6-diisopropylphenyl)-N-(o-tolyl)amine, N-(1-naphthyl) morpholine, N-methyl-N-(1-naphthyl)phenylamine, N-(2-pyridyl)morpholine, N-(2-pyridyl)pipetidine, N-(3-pyridyl) piperidine, N-(3-pyridyl)morpholine, N-N-dibutyl-N-(2-pyridyl)amine, N-methyl-N-phenyl-N-(2-pyridyl)amine, or N-methyl-N-phenyl-N-(3-quinolyl)amine.

39. The process of claim 24, wherein the product of the bond forming reaction is selected from 1-phenyl-2-o-tolylethanone, 1,2-diphenylpropan-1-one, 1-phenyl-2-[4 (trifluoromethyl)phenyl]propan-1-one, 2-phenyl-α-tetralone, 2-(2-methoxyphenyl)-1-phenylpropan-1-one, 1-phenyl-2-(2,4,6-trimethylphenyl)propan-1-one, 2-(o-tolyl)-α-tetralone, 2-(2,6-dimethyl-phenyl)-1-(1-methyl-1H-pyrrol-2-yl)-ethanone, 2-(naphthalen-1-yl)-1-phenyl-propan-1-one, 2-(naththalen-2-yl)-1-phenylpropan-1-one, or 2-(biphenyl-4-yl)-1-phenyl-propan-1-one.

* * * * *

UNITED STATES PATENT AND TRADEMARK OFFICE
CERTIFICATE OF CORRECTION

PATENT NO. : 7,442,800 B2
APPLICATION NO. : 11/441825
DATED : October 28, 2008
INVENTOR(S) : Amoroso et al.

It is certified that error appears in the above-identified patent and that said Letters Patent is hereby corrected as shown below:

Column 49, Line 51, Claim 2, "(trmhd)" should read -- (tmhd) --

Column 50, Line 14, Claim 5, "β-diketimiato" should read -- β-diketiminato --

Column 50, Line 15, Claim 5, "β-ketininato" should read -- β-ketiminato --

Column 51, Line 65, Claim 10, "IMes" should read -- sIMes --

Column 51, Line 67, Claim 10, "idazol" should read -- imidazol --

Column 54, Line 6, Claim 22, "(ifacac)" should read -- (hfacac) --

Column 54, Line 10, Claim 22, "(NHC)Pd(bac)" should read -- (NHC)Pd(bac)$_2$ -- (See the Amendment dated March 11, 2008, page 14, Claim 22, Line 4.)

Column 54, Line 16, Claim 22, "(2,4,6-trethylphenyl)" should read -- (2,4,6-trimethylphenyl) --

Column 54, Line 49, Claim 26, "NBCH2QMs" should read -- NBCH2OMs --

Column 56, Line 10, Claim 36, "iruidazolium" should read -- imidazolium --

Column 56, Line 25, Claim 38, "N-(2-pyridyl)pipetidine" should read -- N-(2-pyridyl)piperidine --

UNITED STATES PATENT AND TRADEMARK OFFICE
CERTIFICATE OF CORRECTION

PATENT NO. : 7,442,800 B2
APPLICATION NO. : 11/441825
DATED : October 28, 2008
INVENTOR(S) : Amoroso et al.

It is certified that error appears in the above-identified patent and that said Letters Patent is hereby corrected as shown below:

Column 56, Line 36, Claim 39, "(naththalen-" should read -- (naphthalen- --

Signed and Sealed this

Fourteenth Day of April, 2009

JOHN DOLL
*Acting Director of the United States Patent and Trademark Office*